(12) United States Patent
Maki

(10) Patent No.: US 6,530,921 B1
(45) Date of Patent: Mar. 11, 2003

(54) LASER IRRADIATION APPARATUS

(75) Inventor: Shin Maki, Kanagawa-ken (JP)

(73) Assignee: Terumo Kabushiki Kaisha, Tokyo (JP)

( * ) Notice: Subject to any disclaimer, the term of this patent is extended or adjusted under 35 U.S.C. 154(b) by 220 days.

(21) Appl. No.: 09/628,326

(22) Filed: Jul. 28, 2000

(30) Foreign Application Priority Data

Jul. 30, 1999 (JP) .......................................... 11-218089
Aug. 12, 1999 (JP) .......................................... 11-228931

(51) Int. Cl.$^7$ ............................................. A61B 18/24
(52) U.S. Cl. ............................................ 606/15; 606/17
(58) Field of Search ............................... 606/15, 16, 13, 606/17

(56) References Cited

U.S. PATENT DOCUMENTS

| | | | |
|---|---|---|---|
| 4,747,405 A | * 5/1988 | Leckrone | 606/7 |
| 4,852,567 A | * 8/1989 | Sinofsky | 606/3 |
| 4,932,956 A | 6/1990 | Reddy et al. | |
| 4,932,958 A | 6/1990 | Reddy et al. | |
| 5,207,672 A | 5/1993 | Roth et al. | |
| 5,292,320 A | 3/1994 | Brown et al. | |
| 5,496,308 A | 3/1996 | Brown et al. | |
| 5,782,824 A | 7/1998 | Abela et al. | |
| 2002/0002370 A1 | * 1/2002 | Levatter | 606/15 |

FOREIGN PATENT DOCUMENTS

| | | | |
|---|---|---|---|
| DE | 3833361 | * | 4/1990 |
| EP | 673 627 | | 9/1995 |
| JP | 2001-46396 | * | 2/2001 |
| WO | 92/04934 | | 4/1991 |
| WO | 9202276 | * | 2/1992 |
| WO | 92/10142 | | 6/1992 |
| WO | 93/04727 | | 3/1993 |

* cited by examiner

Primary Examiner—John A. Jeffery
(74) Attorney, Agent, or Firm—Burns, Doane, Swecker & Mathis, LLP

(57) ABSTRACT

Laser irradiation apparatus 100 comprises: a long and slender main body 101; an optical fiber 107 provided slidable inside the main body 101; a guide unit 115 that forms a curved track, along which the distal end of the optical fiber 107 slides; and a drive unit 109 that causes the optical fiber 107 to reciprocate along the axial direction of the main body 101. The drive unit 109 makes the optical fiber 107 reciprocates within a part of the curved track as a stroke length. The laser rays are irradiated while the distal end of the optical fiber 107 slides along the curved track. The irradiated laser rays crosses the target area, which is the center and its vicinity of a circle that includes the curved track. The areas surrounding the target area are maintained at relatively low temperatures as the laser ray irradiating position is constantly changing. On the other hand, the temperature of the target area rises to a specified temperature because the laser rays concentrate there.

23 Claims, 21 Drawing Sheets

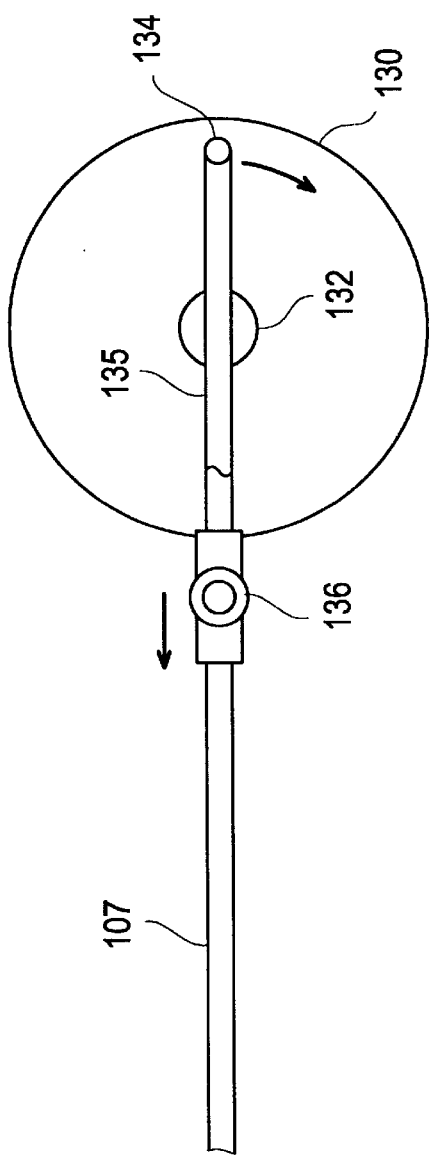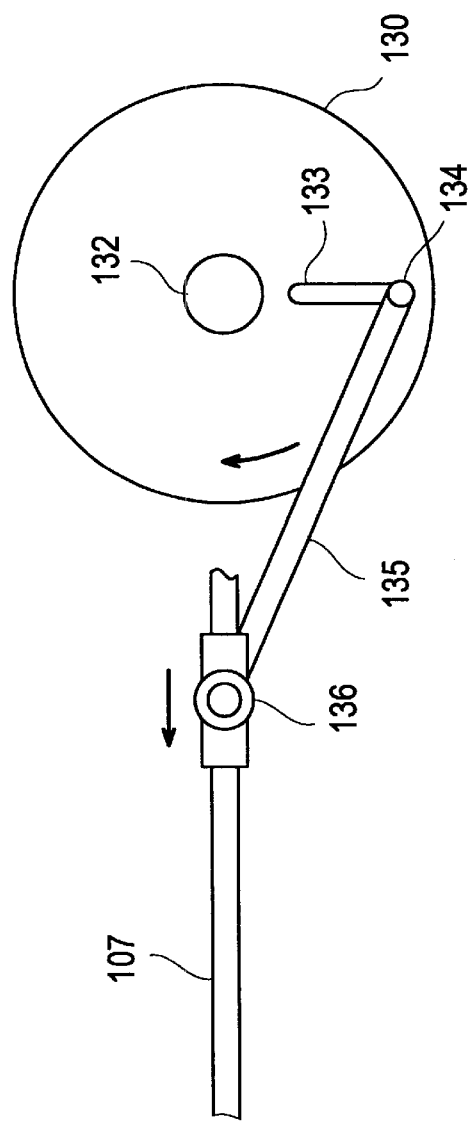
FIG. 9C
FIG. 9D

LASER IRRADIATION APPARATUS

This application is based on application No. 11-218089 and No. 11-228931 filed in Japan, the content of which is hereby incorporated by reference.

BACKGROUND OF THE INVENTION

1. Field of the Invention

This invention relates to a laser irradiation apparatus, in particular, a laser irradiating medical apparatus for treating tumors such as cancer, benign prostatic hyperplasia, etc., by irradiating vital tissues with laser rays, said apparatus being left in vital tissues by means of insertion into vital lumens such as blood vessels, urethras, and abdominal cavities or by means of puncturing organs.

2. Description of the Related Art

A technique of treating lesions by means of laser irradiation apparatuses has been known. The long and slender main body of a laser irradiation apparatus is inserted into a body cavity or a lumen formed by small discission. Lesion tissues are diminished or cleared through alteration, sphacelation, coagulation, cauterization and evaporation by means of irradiating the lesions with laser rays.

The technique is generally to irradiate directly a lesion existing on the surface layer of a vital tissue or its vicinity. However, in order to apply this technique to a deep lesion, heating the lesion to a sufficient temperature, it is necessary to irradiate it with a laser ray of a relatively high power. As a result, there may be a case of or a concern for damaging normal tissues adjacent to the lesion, such as the surface layer.

WO93/04727 discloses a technique for coagulating and diminishing a part of a tumor or prostate by means of laser irradiation. This technique is to infuse a coolant into a balloon in order to heat only the internal tumor or the prostate without heating the surface of the urethra that is adjacent to the balloon. Laser ray is irradiated from a fixed laser irradiator in this device. Consequently, it is necessary to use a low-power laser ray so as not to heat the surface of the urethra, thus requiring a long irradiation time.

U.S. Pat. No. 5,292,320 discloses an apparatus for treating benign prostatic hyperplasia transurethrally using laser rays. In this apparatus, multiple irradiation units placed at different positions irradiates laser rays simultaneously. The irradiated laser rays are converged on a target point in a deep legion to generate a sufficient heat for heating and diminishing the legion tissue. Consequently, the temperature in the vicinity of the target point becomes higher than other parts where the laser rays do not converge. However, since the light paths of the laser rays are fixed, certain areas are formed where the temperatures are slightly higher than normal in the vicinity of the surface layer where no convergence of laser rays are occurring. This phenomenon provides an ill affect on the protection of the surface. Therefore, it is not satisfactory from the point of treating only a deep lesion while preventing damages on the surface layer.

SUMMARY OF THE INVENTION

The object of this invention is to provide an apparatus that effectively irradiates a target area with laser rays, particularly a target area hidden deep inside a vital tissue, while securely preventing damages to normal tissues, particularly, a normal surface tissue that is in contact with the laser irradiation apparatus.

In one aspect of the invention, it is a laser irradiation apparatus, comprising:
- a long and slender main body;
- an optical fiber slidably provided inside the main body, which accepts incident laser rays through its proximate end and emits said laser rays sideways or diagonally through its distal end; and
- a guide unit that forms a curved track for a tip of the optical fiber to slide.

According to the laser irradiation apparatus, the laser rays from the emitting position that continually moves concentrates on the target area so that the temperatures of the areas other than the target area are maintained lower. This prevents or reduces damages of the areas other than the target area. Moreover, since the damage on the surface where a contact is made with the apparatus can be prevented even in a case where the target area is hidden deep inside the tissue, it provides a better safety to the patient. Further, the apparatus provides a combination of the reciprocating motion of the emitting area and the change of the emitting angle by means of the reciprocating motion of the optical fiber alone. Therefore, it has advantages such that it has a simpler structure, can be manufactured easily and is less likely to break down.

In another aspect of the invention, it is a laser irradiation apparatus, comprising:
- a long and slender main body;
- a flexible curving part provided on the distal end of the main body;
- an optical fiber slidably provided inside the main body and the curving part, which accepts incident laser rays through its proximate end and emits the laser rays sideways or in diagonal directions through its distal end; and
- a curve operating mechanism that forms a curved track for a tip of the optical fiber to slide by curving the curving part.

According to the laser irradiation apparatus, it is possible to irradiate effectively a target area with laser rays, particularly a target area hidden deep inside a vital tissue, while securely preventing damages to normal tissues, particularly, a normal surface tissue that is in contact with the laser irradiation apparatus. Moreover, it has advantages such that it has a simpler structure, can be manufactured easily and is less likely to break down.

The objects, features, and characteristics of this invention other than those set forth above will become apparent from the description given herein below with reference to preferred embodiments illustrated in the accompanying drawings.

BRIEF DESCRIPTION OF THE DRAWINGS

FIGS. 9A–9D are drawings for describing the operating condition of the drive unit;

DETAILED DESCRIPTION OF THE PREFERRED EMBODIMENT

The laser irradiation apparatus of the present invention will be described below in detail referring to the preferred embodiments shown in the attached drawings.

Embodiment 1

Figure 1:
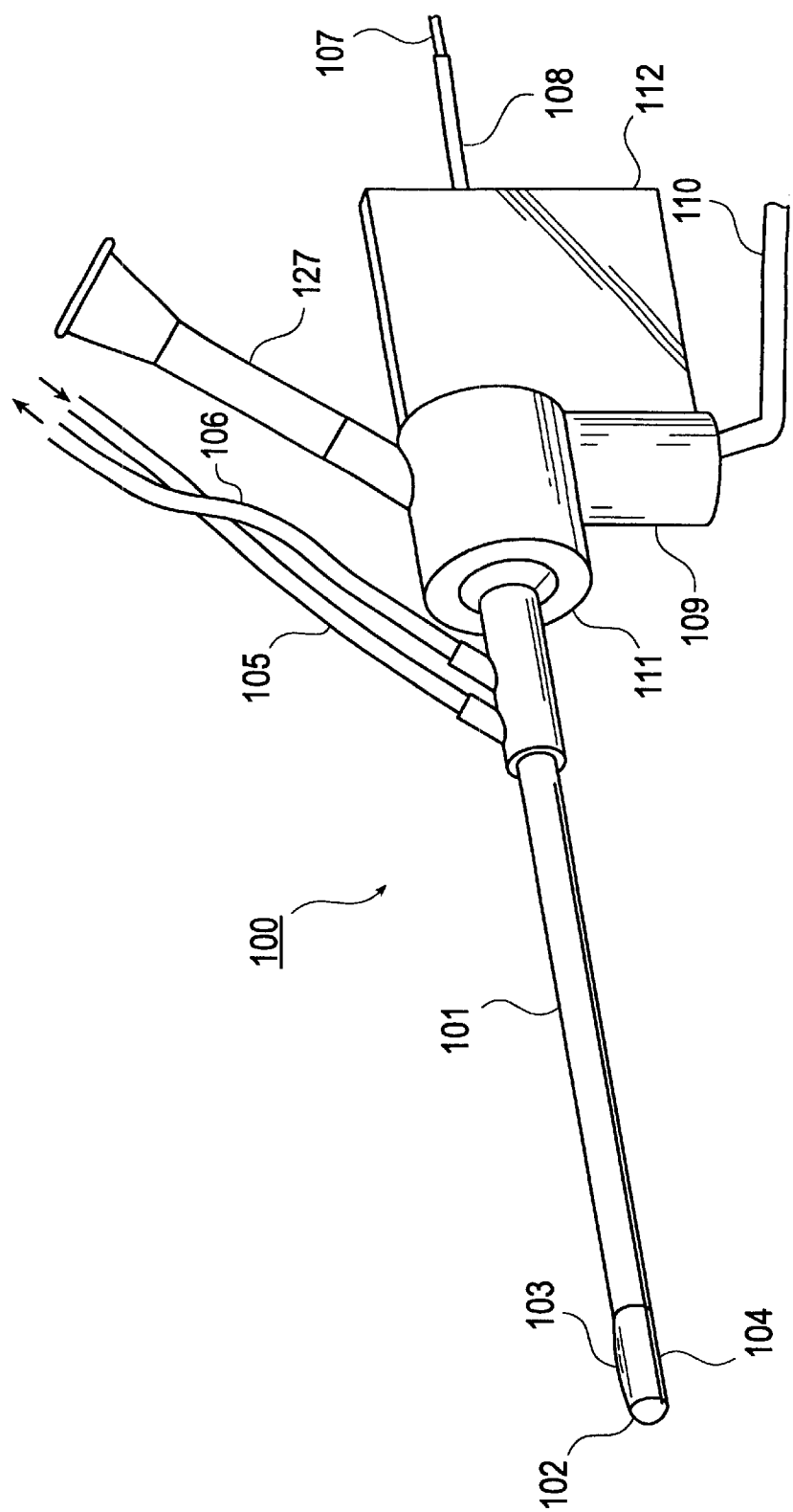
FIG. 1 is a perspective view of a laser irradiation apparatus according to a first embodiment of the present invention.
Figure 2:
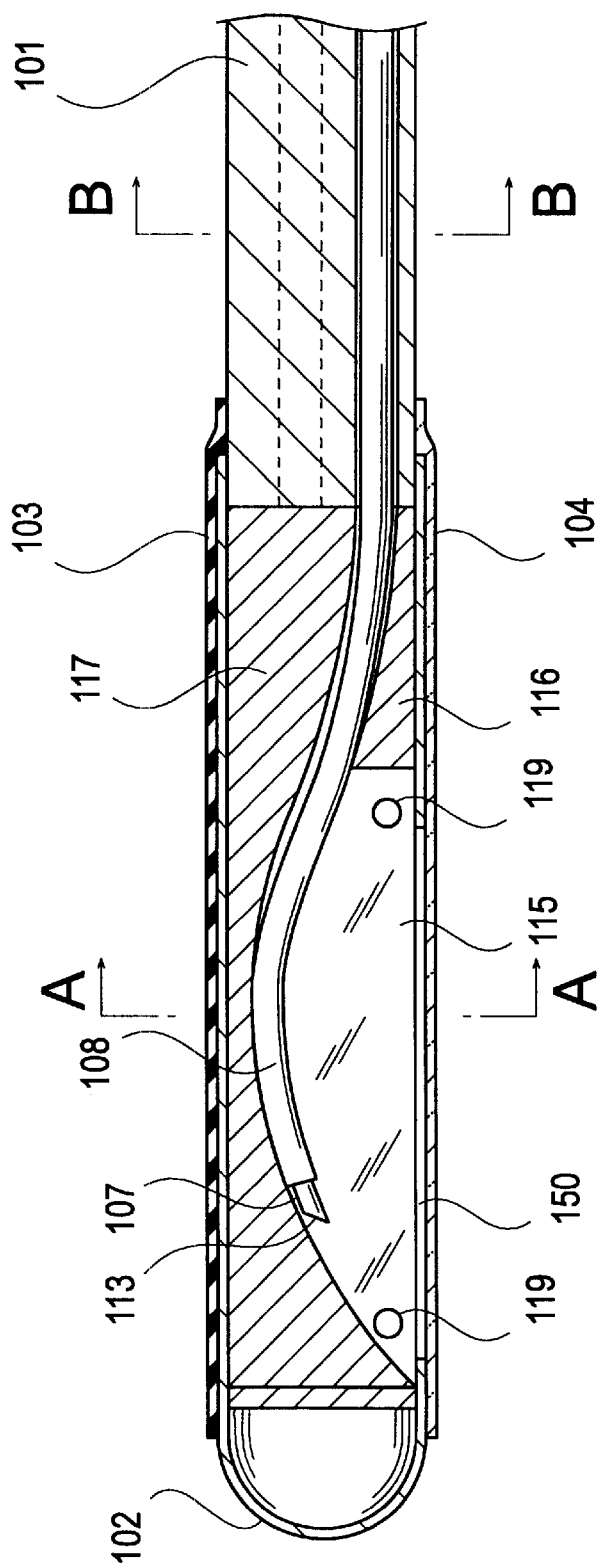
FIG. 2 is a cross-sectional view of the distal end of the laser irradiation apparatus of the first embodiment.
Figure 3:
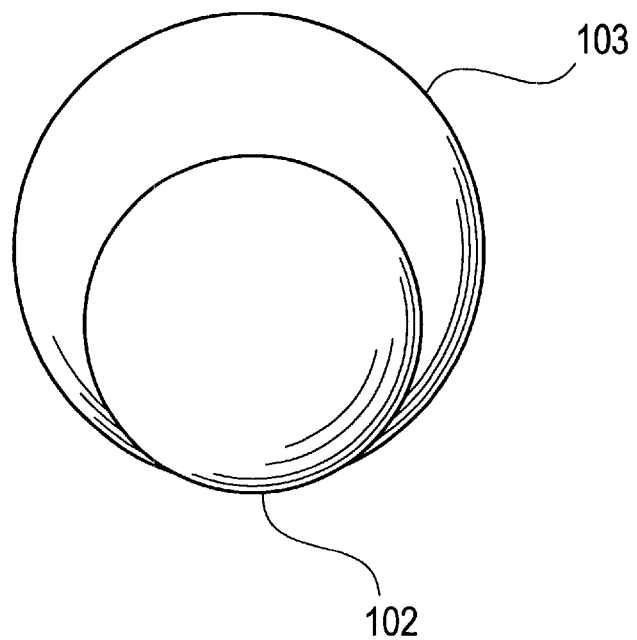
FIG. 3 is a front elevational view of the expanded condition of the balloon of the laser irradiation apparatus of the first embodiment.

The laser irradiation apparatus 100 shown in FIG. 1 and FIG. 2 is a side shooting type laser irradiation apparatus that irradiates vital tissues with laser rays. The laser irradiation apparatus 100 is typically used for treating benign prostatic hyperplasia. The laser irradiation apparatus 100 has a long and slender main body 101 that consists of a tube like member. The distal end of the main body 101 is provided with a housing 102 comprising a hard tube-like member. The housing 102 has a window 150 that transmits laser rays. The end of the housing 102 is sealed. The surface of the housing 102 is provided with multiple small holes that are not shown in the drawing. An inflatable balloon 103 is provided surrounding the housing 102. The balloon 103 is made of a plastic film and can expand except in the area of the window 150. The balloon 103 expands by injecting or circulating cooling water in the housing 102. The balloon 103 performs the function of pressing the window 150 side to the surface of a vital tissue. A light permeable cover 104 is adhered and fixed to the periphery of the window 150 of the housing 102. A expanded condition of the balloon 103 is shown in FIG. 3.

The cooling water circulates through the main body 101 under pressure in order to cool the surface of the vital tissue that receives laser rays, the laser-shooting end of the housing 102, etc. The cooling water is circulated by the coolant circulating device (not shown). In FIG. 1, "105" is a cooling water supply tube and "106" is a cooling water drain tube.

An optical fiber 107 that transmits laser rays is provided inside the main body 101 and the housing 102. The optical fiber 107 is covered with a protective tube 108 except its distal end. The proximate end of the optical fiber 107 is connected to the laser ray generator (not shown).

The optical fiber 107 is linearly reciprocated by a drive unit 109. The drive unit 109 is preferably an electrical device, such as a motor. The rotary motion of the motor is converted into a linear reciprocating motion by means of a cam device, etc. In FIG. 1, "110" is an electrical cable and "111" is a cam box.

Next to the drive unit 109 is provided a cushioning device 112, in which the optical fiber 107 is stored in a loop. The reciprocating motion of the optical fiber 107 by means of the drive unit 109 is converted into an expansion-contraction motion of the loop inside the cushioning device 112. The motion and the load of the optical fiber 107 are absorbed by the cushioning device 112. Therefore, the optical fiber 107 does not move excessively outside the laser irradiation apparatus 100.

Figure 4:
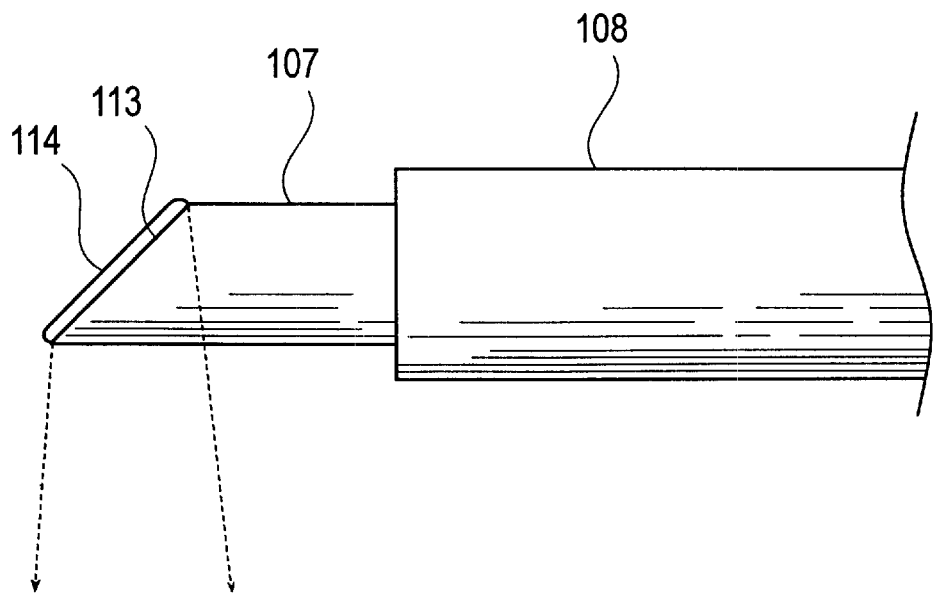
FIG. 4 is a view of the distal end of the optical fiber of the first embodiment.

A fiber tip 113 located inside the housing 102 is constituted in such a way as to be able to emit laser rays sideways or diagonally. Refer to FIG. 4, in the first embodiment, the fiber tip 113 has a flat face cut to an angle of about 35–50 degrees, preferably 45 degrees, relative to the axis of the optical fiber. The surface of the flat face is coated with a reflective film 114. The reflective film 114 is preferably a metallic film, such as a gold film, formed by vapor-depositing or plating. A dielectric substance multi-layer film formed by reciprocally vapor-depositing high reflection ratio dielectric substances such as $Al_2O_3$, $ZrO_2$, $TiO_2$ and $CeO_2$, and low reflection ratio dielectric substances such as $MgF_2$ and $SiO_2$ in multiple layers can be also preferably used. The thickness of the reflective film 114 is preferably 0.2–1 $\mu$m. The laser rays transmitted through the optical fiber 107 are reflected by the reflection film 114 at the fiber tip 113 to be emitted sideways from the fiber (arrow direction shown in FIG. 4).

Figure 5:
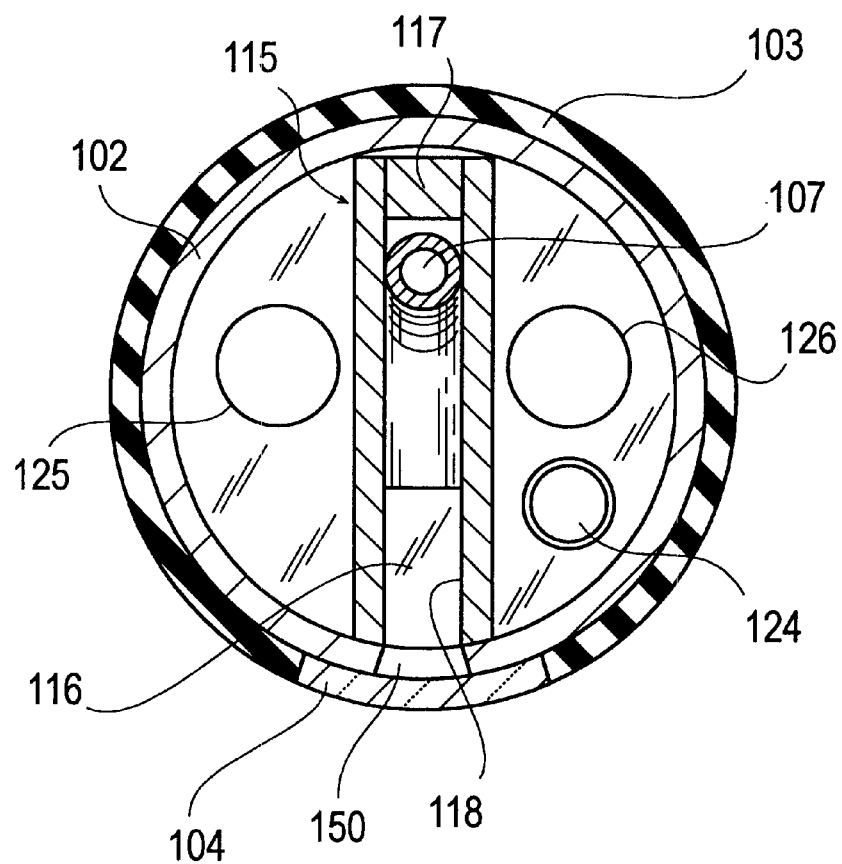
FIG. 5 is a cross-sectional view along the line A—A of the laser irradiation apparatus shown in FIG. 2.

In FIG. 5, a guide unit 115 that regulates the path of the optical fiber 107 that moves reciprocally comprises a box-shaped member affixed to the inside of the housing 102. The guide unit 115 consists of a first guide 116 and a second guide 117. The first guide 116 guides the optical fiber 107 to point it upward in FIG. 2 while the optical fiber 107 is reciprocating. The second guide 117 guides the optical fiber 107, which is pointing upward, to be on the arc-shaped track as it performs a reciprocating motion. The bottom side of the guide unit 115 has an opening, which serves as a laser ray emitting window. In order to emit the laser rays effectively, it is preferable to coat the laser ray transmitting part 118 on the inside of the guide unit 115 with a reflective film for reflecting the laser rays. The reflective film can be one that is similar to the reflective film 114 of the fiber tip 113. An opening 119 is provided on the laser transmitting part 118 to allow the cooling water to circulate. It is preferable that the opening 119 is located outside of the stroke range of the reciprocating fiber tip 113 so that the laser rays do not pass through the area where the opening 119 is located.

Figure 6:
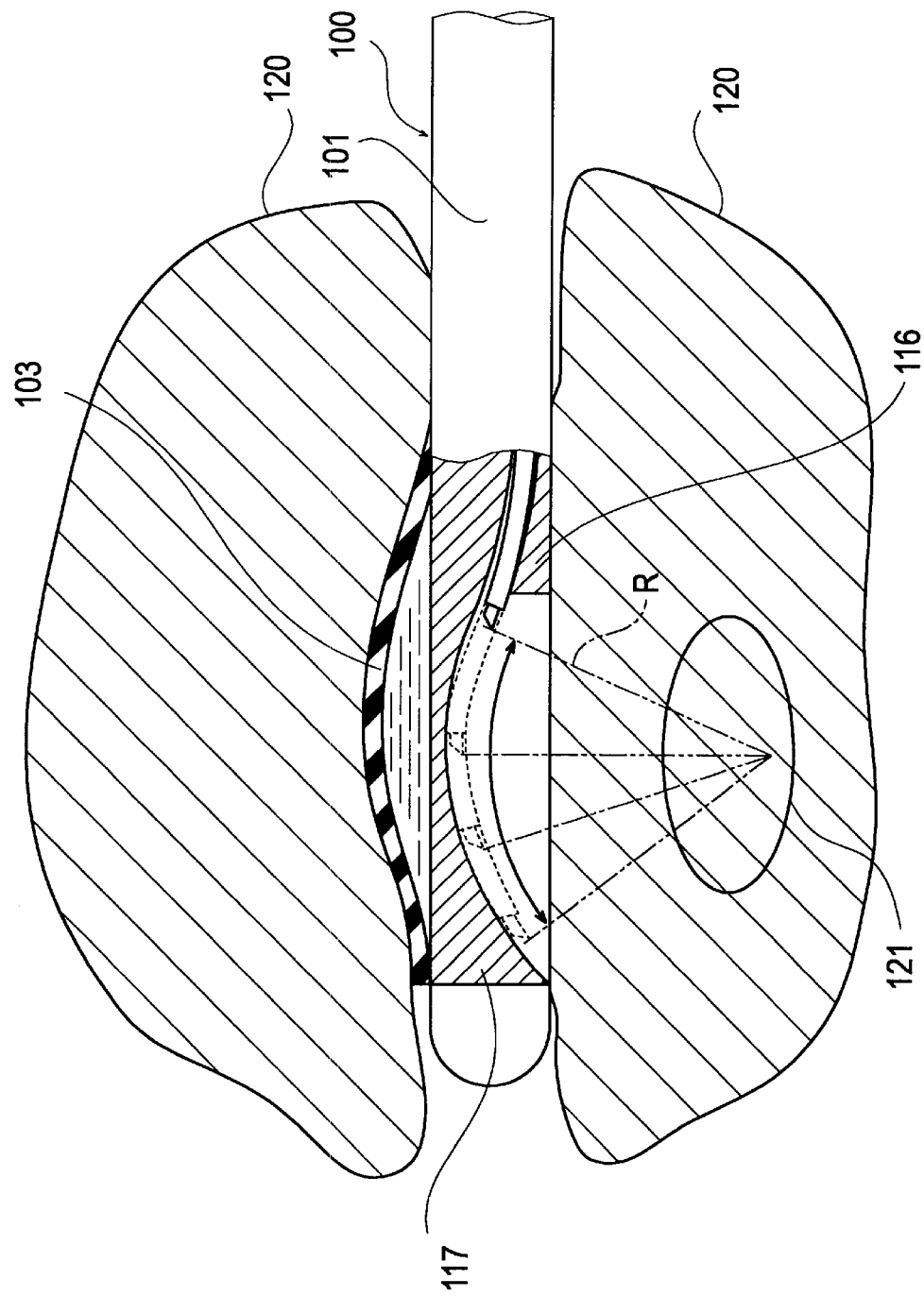
FIG. 6 is a conceptual drawing for describing the operating condition of the laser irradiation apparatus shown in FIG. 1.

FIG. 6 is a conceptual diagram of an actual treatment for describing how the laser ray emitting direction changes as the optical fiber 107 reciprocates. Parts other than the optical fiber 107 and the guide unit 115 are simplified in FIG. 6.

A prostate cross section 120 is shown in FIG. 6. The laser emitting part of the laser irradiation apparatus 100 inserted into the urethra makes a close contact with the surface of the urethra as the balloon 103 expands.

The fiber tip 113, which is the laser ray emitting part of the optical fiber 107, reciprocates within the range shown by the arrow in the figure. The fiber tip 113 has to be located further toward the distal end than the first guide 116 when the fiber tip 113 is positioned closest to the proximate end. It is preferable that, when the fiber tip 113 is positioned closest to the distal end located, it is at a position not beyond the distal end of the second guide 117 and simultaneously the laser rays do not pass through the opening 119. The laser rays are emitted from the fiber tip 113 sideways (preferably in about a vertical direction) relative to the axial direction of the optical fiber 107. The axial direction of the optical fiber 107 is the tangential direction of the arc formed by the second guide 117 regardless of the position of the fiber tip 113. Therefore, the laser emitting direction is always toward approximately the center (target area 121) of a circle that includes this arc. Consequently, if the laser rays are irradiated while the optical fiber 107 is reciprocating, the irradiation time and hence the generated heat are limited on the surface of the vital tissue, to which the laser irradiation apparatus 100 is contacting, as the laser emitting position is constantly moving. On the other hand, the irradiation time is long and hence the generated heat is greater at the target area 121, which is located deep in the vital tissue and where the laser rays converge. Therefore, it is possible to heat and treat only the deep target area while preserving the surface area of the vital tissue.

The arc that the fiber tip 113 generates is smaller than a half circle, preferably 8–25% of the circle, where a half circle being 50%. The radius R of the arc should be adjustable according to the diameter of the main body 101 and the depth of the target area to be treated. In case of an apparatus intended for the treatment of benign prostatic hyperplasia as shown in the embodiment, the diameter of the main body 101 is about 5–8 mm, and the depth of the target area is preferably about 10–20 mm. As an example, if the outside diameter of the main body 101 is 7 mm, and the depth of the target area from the urethra is approximately 15 mm, the radius of the arc becomes approximately 21 mm, so that approximately 20% of the circle is covered by the reciprocating movement.

Figure 7:
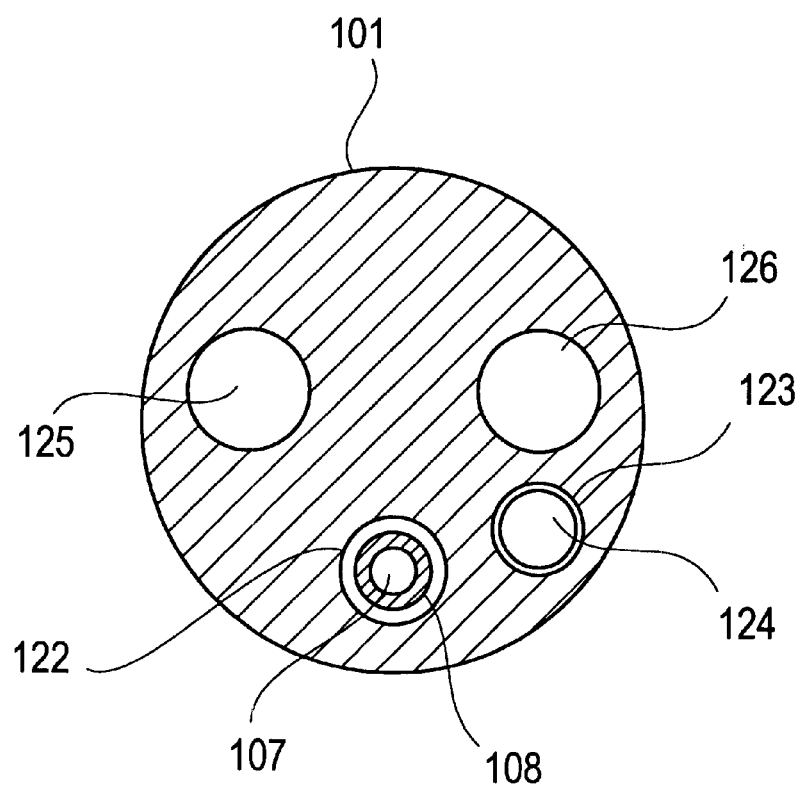
FIG. 7 is a cross-sectional view along the line B—B of the laser irradiation apparatus shown in FIG. 2.

In FIG. 7, "122" is a lumen, through which the optical fiber 107 covered with a protective tube 108 can reciprocate. The lumen 122 is formed parallel with the axis of the main body 101. An O-ring (not shown) is provided as a seal between the protective tube 108 and the lumen 122 to prevent leakage of the cooling water at the proximate end of the lumen 122. A lumen 123 is provided for an endoscope 124. In this figure, "125", is a supply lumen for the cooling water, "126" is a discharge lumen for the cooling water. These lumens 125 and 126 are connected with the tubes 105 and 106 shown in FIG. 1 to be further connected with the cooling water circulating apparatus (not shown). It is preferable to prevent the back flow of the cooling water by providing a check valve at the proximate end of each of the lumens 125 and 126.

The endoscope 124 consists of a bundle of optical fibers and a protective tube, and has an image formation lens (not shown) at the distal end. The endoscope 124 is provided in such a way as to be able to move freely in and out of an endoscope insertion port 127 provided at the proximate end of the laser irradiation apparatus 100. By observation using the endoscope, the positioning of the housing 102 and the laser irradiation position can be visually confirmed. As the irradiation surface can be continuously observed during the laser irradiation, the irradiation condition can be optimized based on the actually observed condition.

Figure 8:
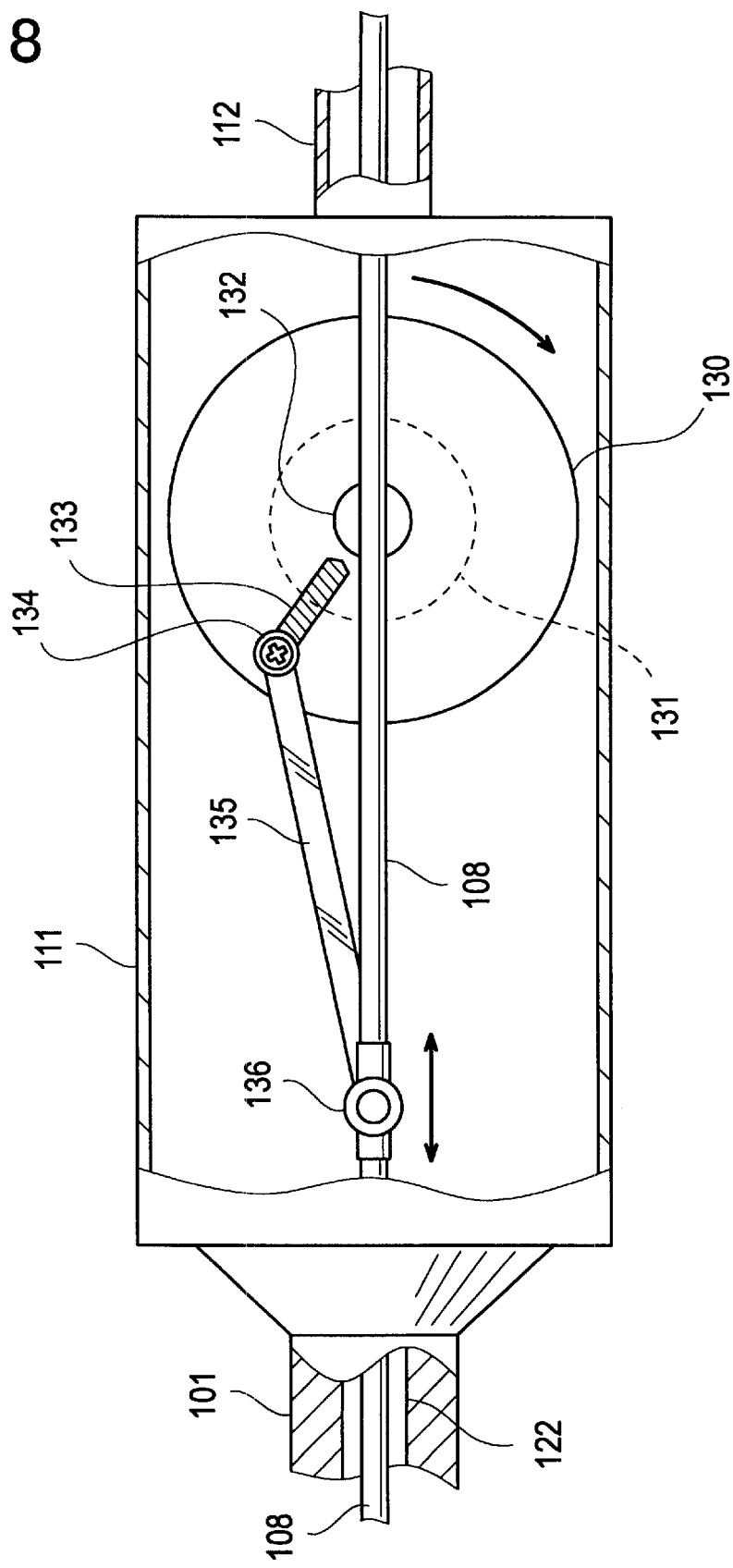
FIG. 8 is a partially cut out view of the drive unit of a laser irradiation apparatus.
Figure 9A:
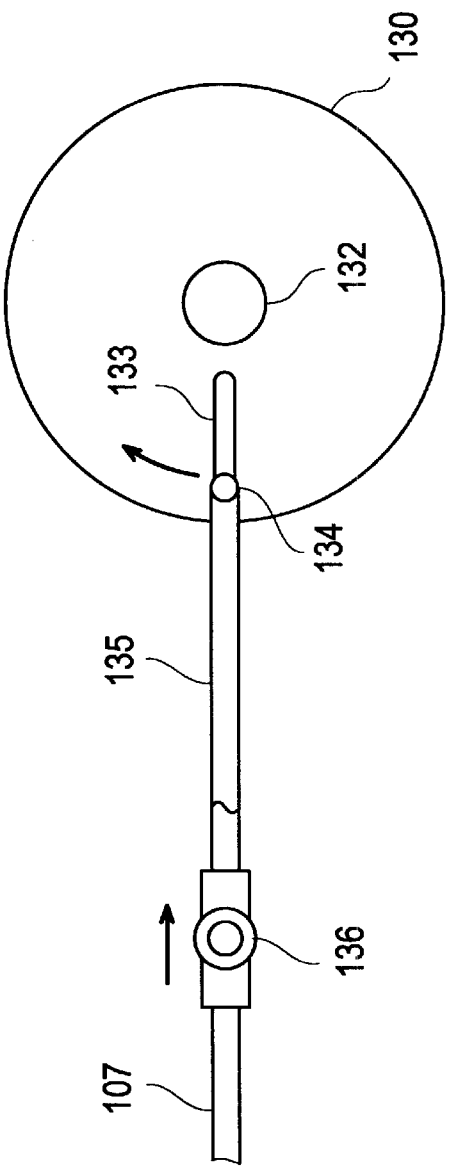
Figure 9B:
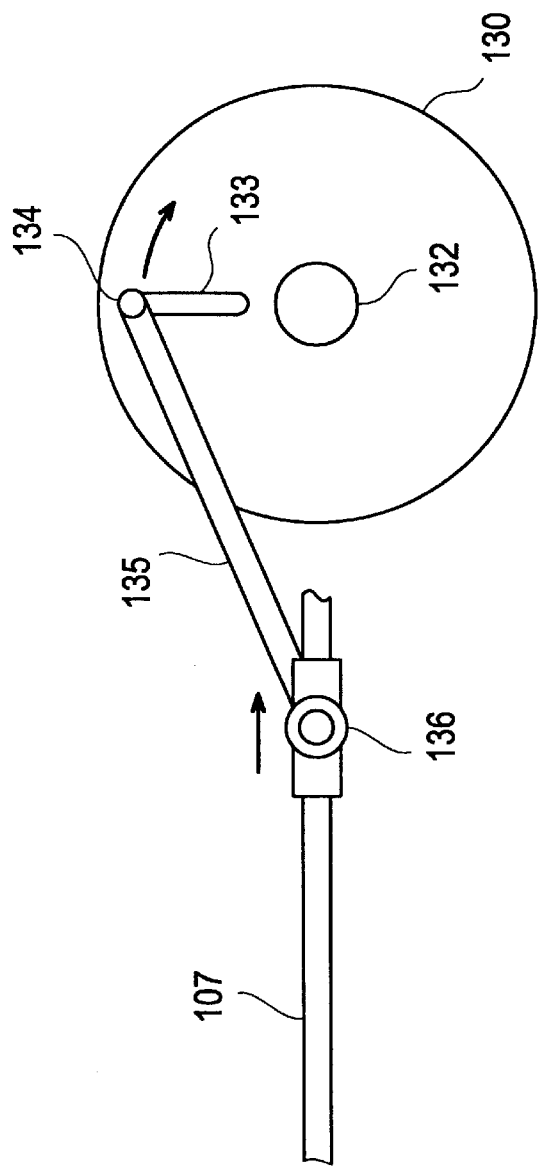

The optical fiber 107 is held in the cam box 111 for the reciprocating motion. FIG. 8 is to show the mechanism for reciprocating the optical fiber 107. A rotor 130 is provided to rotate freely within the cam box 111. The rotating member 130 has a shaft 132 that is connected to the output shaft of the motor 131 provided in the drive unit 109. As the motor 131 rotates, the rotating member 130 rotates. The surface of the rotor 130 has a groove 133 that extends radially relative to the shaft 132. A joint 134 with a threaded member is positioned to be able to move within the groove 133. By tightening the threaded member, the joint 134 is positioned at a certain position along the groove 133 and affixed with the rotor 130. One end of the rod 135 is pivotally connected to the joint 134. The rotor 130 is connected to one end of the rod 135 via the joint 134. A gripping joint 136 is provided in the middle of the protective tube 108, into which the optical fiber 107 is inserted and fixed. The gripping joint 136 grips the optical fiber 107 through the protective tube 108 within the cam box 111. The other end of a rod 135 is connected rotatably to the gripping joint 136. The reciprocation range of the optical fiber 107 is adjusted by moving the affixed position of the joint 134 radially along the groove 133 to change the rotating radius of the joint 134.

The optical fiber 107 covered by the protective tube 108, as mentioned before, is slidably supported in the lumen 122 of the main body 101. The optical fiber 107 is pivotally connected with the rod 135 via the gripping joint 136 near the entrance to the lumens 122 in the cam box 111 and extends through the cam box 111 into the cushioning device 112.

FIG. 9A through FIG. 9D are drawings for describing the rotating motion of the rotor 130 driven by the motor 131 and the reciprocating motion of the optical fiber 107 caused thereby, where a portion of the optical fiber 107 and the protective tube 108 are eliminated for the sake of the description. As shown in FIG. 9A through FIG. 9D, the rotor 130 rotates around the shaft 132 due to the rotation of the motor 131, which causes the optical fiber to reciprocate along the axial direction of the main body 101 between the position indicated by FIG. 9A and the position indicated by FIG. 9C. Therefore, the stroke, i.e., the range of the reciprocating motion, of the fiber tip 113 is twice the rotating radius of the joint 134.

Next, the specific usage condition and operation of the laser irradiation apparatus 100 will be described.

First, as shown in FIG. 6, insert the main body 101 into the urethra with the distal end leading, and position the housing 102 provided at the distal end in the vicinity of the legion, i.e., the target area 121 of the prostate 120. It is preferable to confirm the position of the housing 102 by means of direct observation with the use of the endoscope 124. Next, adjust the positional relation between the laser ray emitting part and the target area 121 by moving the entire laser irradiation apparatus 100 in the specified direction (lengthwise direction of the main body 101) or rotating the entire laser irradiation apparatus 100 manually while observing it with the endoscope 124.

Next, activate the coolant circulation apparatus (not shown) to circulate the cooling water through the laser irradiation apparatus 100 and expand the balloon 103 to a specified size. More specifically, the cooling water flows into the housing 102 via the cooling water supply tube 105 and the supply lumen 125, and into the balloon 103 through multiple holes provided on the side wall of the housing 102 to expand the balloon 103.

As a result of the expansion of the balloon 103, the window 150 side of the housing 102, i.e., opposite side of the balloon, is pressed against and forms a close contact with the surface layer of the urethra to be affixed there. This solidifies the positional relation between the laser ray emission area and the target area 121. Thus, the direction of the target area and the depth will be fixed to the condition the operator intended, and the sure irradiation of the laser rays on the target area within the vital tissue becomes possible. The area where the contact with the cover 104 occurs and its vicinity, i.e., the surface layer of the vital tissue will be cooled with the cooling water. The damage of the surface layer can be more securely prevented.

After fixing the position of the housing 102, activate a laser ray generator (not shown) as well as the motor 131 simultaneously. The laser rays generated by the laser ray generator are guided through the optical fiber 107, reflected by the reflective film 114 at the fiber tip 113 sideways relative to the axis of the optical fiber 107, emitted through the window 150, and irradiated on the target area 121. In the meanwhile, the fiber tip 113 reciprocates axially with a frequency of approximately 0.1–10 Hz, preferably 1–6 Hz, changing the emitting angle. As a result, each axis of the laser ray passage changes continuously but all axes is crossed at the target area 121 or a just below point thereof.

Consequently, the target area 121 and its vicinity of the vital tissue 120 will be heated by the laser rays and reached to desired temperature. On the other hand, the irradiation time of the upper area located above the target area 121 in FIG. 6, i.e., the surface layer of the vital tissue 120, is short, so that the area is maintained at a relatively low temperature and is protected from the effect of the laser rays. Similarly, the laser ray irradiation time for the area located below the target area in FIG. 6 is short, so that the heat generation is small. In other words,the temperatures of the areas surrounding the target area 121 are maintained relatively low and protected from the effects of the laser rays. Since the damages to the areas other than the target area 121 are prevented or reduced, the apparatus 100 has a high safety characteristic against the patient. It is useful as it prevent the surface layer damage even if the target area 121 is located deep inside the vital tissue.

Next, a different position is selected as the target area 121 and the laser irradiation is performed. By repeating this treatment, multiple areas to be treated can be heated.

The laser rays to be used on the laser irradiation apparatus 100 of the present embodiment can be of any kind as long as it can reach a certain depth of the vital tissue. However, the wavelength is preferably 750–1300 nm or 1600–1800 nm. Since laser rays with the wavelengths of 750–1300 nm or 1600–1800 nm provide excellent depth penetration capabilities its energy is not absorbed much in the surface layer, so that it is possible to irradiate the target area (legion) lying in the deep area of the vital tissue more effectively.

Laser generators that generate laser rays of such ranges of wavelengths include gaseous laser generators such as He—Ne laser generators, solid lasers such as Nd-YAG lasers, and semiconductor lasers such as GaAlAs lasers.

Structural materials for the main body 101 and the housing 102 can be a polymer alloy containing at least one of the followings or a polymer material including multiple ingredients from the followings: polycarbonate; acryl; polyolefin such as polyethylene and polypropylene; ethylene-vinyl acetate copolymer (EVA); polyvinyl chloride; polyester such as polyethylene terephthalate and polybutylene tereph-thalate; polyamide; polyurethane; polystyrene; and fluorocarbon resin. Further, the properties of these ingredients should be excellent optical transmissivity in order not to be interfered with the visual field for an endoscope 124.

The surface of the main body 101 or the balloon 103 can be coated with lubricating materials such as hydrophilic polymer materials, silicon and fluoro carbon resin. They will reduce the friction of the main body surface, and make it smoother to insert it into body cavities. It is also possible to use a throwaway sheath to cover the main body and apply lubricating coating to the sheath surface. The potential shortcoming of deterioration of lubricating capability due to wear after multiple uses can be prevented by means of using a throwaway sheath.

Hydrophilic polymers that can be preferably used for lubrication coating include: carboxymethyl cellulose, polysaccharide, polyvinylalcohol, polyethylene oxide, polyacrylate soda, methylvinylether-maleic anhydride copolymer, and water soluble polyamide. Of these, methylvinylether-maleic anhydride copolymer is most preferable.

When a laser irradiation apparatus 100 equipped with a main body 101 coated with a hydrophilic polymer is used, the main body 101 can be immersed into physiological saline. This brings wetness of the surface layer of the main body 101 and the laser irradiation apparatus 100 comes to have lubricity. In other words,if the laser irradiation apparatus 100 has a surface layer containing a hydrophilic polymer, the friction resistance between the vital tissue and the laser irradiation apparatus 100 reduces. This reduces the burden of the patient and increases the safety. For example, insertion of the laser irradiation equipment 100 into a body cavity or its extraction from a body cavity or its transportation and rotation within a body cavity can be performed more smoothly.

The cover 104 should preferably be made of materials with excellent optical transmissivity such as PET, quartz glass, acryl, polystyrene, polycarbonate, polyethylene, polypropylene, vinylidene chloride, Teflon®, and polyester.

The protective tube 108 that covers the optical fiber 107 should preferably be made of fluorocarbon resins such as PTFE.

Embodiment 2

Next, it is described a second embodiment of the energy irradiation apparatus according to the invention. Since the second embodiment is different from the first embodiment only in the structure at the optical fiber tip for reflecting the laser light, only the difference will be described below.

Figure 10:
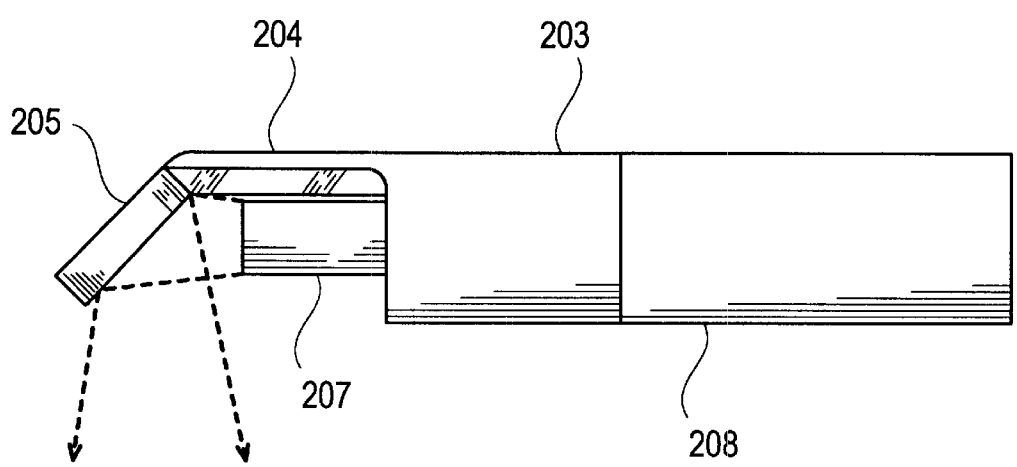
FIG. 10 is a view of the distal end of the optical fiber of the laser irradiation apparatus of a second embodiment.

FIG. 10 is a side view of the distal end of an optical fiber 207 used in the laser irradiation apparatus 100 according to the second embodiment of the invention. In FIG. 10, "208" is a protective tube of the optical fiber 207. A mirror supporting part 203 is provided abutting with the distal end of the protective tuber 208. The mirror supporting part 203 supports a reflective mirror 205 via an arm 204. The reflective mirror 205 is preferably provided to be slanted about 45 degrees relative to the lengthwise direction of the optical fiber 207.

In the second embodiment, the laser rays irradiated from the distal end of the optical fiber 207 is reflected by the reflective mirror 205 into a direction approximately perpendicular to the lengthwise direction of the optical fiber 207. The reflective surface of the reflective mirror 205 is preferably a metal film formed by vapor deposition or plating as in the case of the reflective film 114 of the first embodiment or a dielectric multi-layer film. The second embodiment is advantageous over the first embodiment, which uses a direct reflective film provided on the fiber tip, in that the heat generation at the contact surface between the distal end and the reflective film is minimized.

Embodiment 3

Next, it is described a third embodiment of the energy irradiation apparatus according to the invention. Since the third embodiment is different from the first embodiment only in that the guide unit 115 is simplified, only the difference will be described below.

Figure 11:
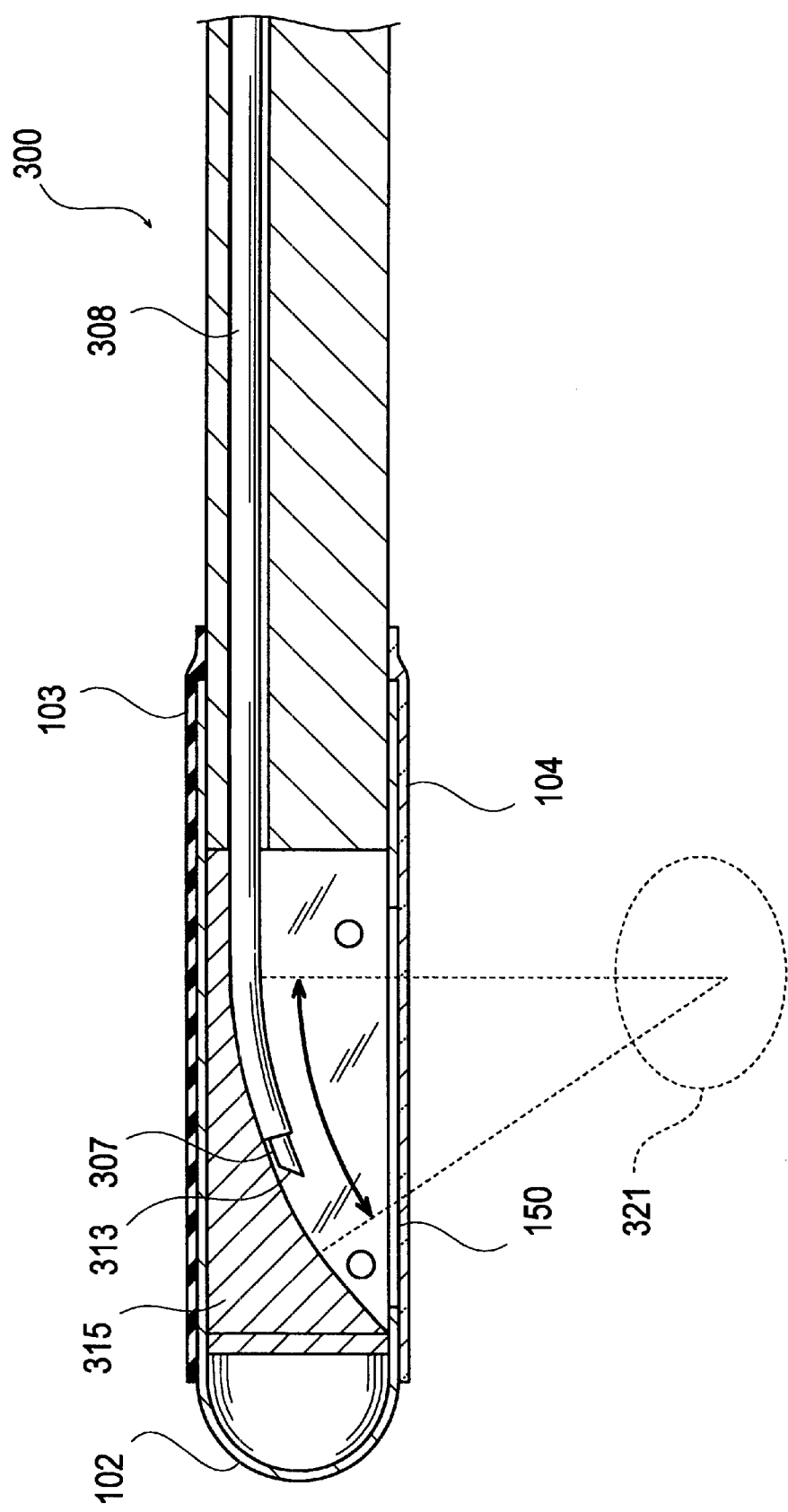
FIG. 11 is a cross-sectional view of the distal end of the laser irradiation apparatus of a third embodiment.

FIG. 11 is a cross section showing the distal end of the third embodiment of the energy irradiation apparatus 300 according to the invention. In FIG. 11, those items that are functionally identical to those in the first embodiment are identified by using the same symbols.

In FIG. 11, a guide unit 315 guides the fiber tip 313 while the optical fiber 307 covered by the protective tube 308 reciprocates. Thanks to the guide unit 315, the reciprocation track of the optical fiber 307 is formed in an arc-like shape that is bending toward the irradiation direction of the laser rays (downward in the figure). In the third embodiment, the range of the reciprocating stroke of the optical fiber 307 is as shown by the arrow in the figure. A reflective film (not shown) similar to the one used in the first embodiment is provided at the fiber tip 313. This allows the optical fiber 307 to irradiate the laser rays in a direction perpendicular to the axial direction of the optical fiber 307.

In the third embodiment, the fiber tip 313 reciprocates along an arc-like track provided by the guide unit 315. The laser ray emitting position is constantly changing within the range shown by the arrow in the figure. The laser rays are always aimed at the target position 321, which is the center of the arc. Therefore, the laser rays are continuously irradiated the target position 321, while the surface of the vital tissue directly in contact with the emitting surface of the laser irradiation apparatus 300 is only intermittently irradiated. Thus, it is possible to heat the target position hidden deep inside the tissue sufficiently without unnecessarily heating the surface of the vital tissue that comes in contact with the apparatus 300. According to the third embodiment, it is possible to simplify the structure of the guide unit and miniaturize the portion of the laser irradiation apparatus inserted into the patient's body. It is also possible to reduce the sliding resistance of the optical fiber.

Embodiment 4

Next, it is described a fourth embodiment of the energy irradiation apparatus of the invention. The fourth embodiment has a guide unit with a structure identical to that of the guide unit 115 of the first embodiment but with a change in the reflective surface of the optical fiber, only the difference will be described below.

Figure 12:
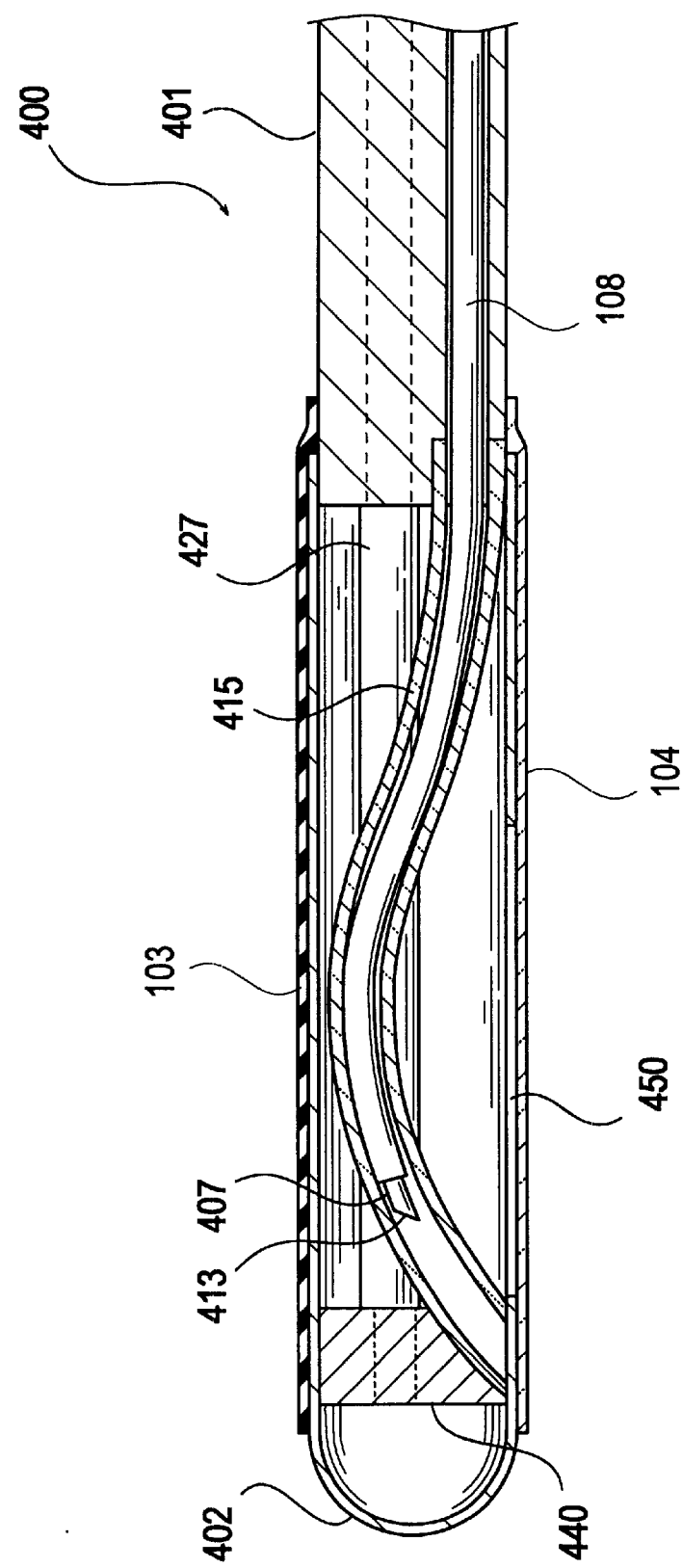
FIG. 12 is a cross-sectional view of the distal end of the laser irradiation apparatus of a fourth embodiment.

FIG. 12 is a cross section of the distal end of the laser irradiation apparatus 400 according to the fourth embodiment of the invention. In FIG. 12, those items that are functionally identical to those in the first embodiment are identified by using the same symbols. The fiber tip 413 of an optical fiber 407 shown in FIG. 12 forms a flat face slanted approximately 45 degrees against the axial direction of the optical fiber 407. However, no reflective film is provided as in the first embodiment. A guide unit 415 is made of a light transmitting hard tube and is sealed from the surrounding. Therefore, the inside of the guide unit 415 can be filled with a gas such as air even if the inside of a housing 402 is filled with a coolant. The guide unit 415 is affixed with the distal end of the main body 401 inside the housing 402 by means of a fixture 440. Since a fiber tip 413 is surrounded by a gas such as air or an inert gas, the laser rays are reflected by the flat face of the fiber tip 413 due to a difference in the refractive indexes of the inside of the optical fiber 407 and the surrounding gas, and the laser rays will be emitted sideways relative to the optical fiber. The gas to be filled should preferably be circulated in order to prevent heating of the optical fiber 407 by the laser rays.

A drainpipe 427 for circulating the coolant passes through the housing 402 and extends up to the fixture 440. The drainpipe 427 opens at the distal end of the fixture 440. The cooling water is supplied by the cooling water supply tube 105 also in this fourth embodiment same as in the first embodiment shown in FIG. 1, flows through a lumen in the housing 401 into the housing 402 at the proximate end of the housing 402. The cooling water expands a balloon and cools a laser ray emitting window 450 and the guide unit 415. The cooling water then flows into the distal end of the housing 402 through an opening provided at the fixture 440 and is drained through the drain pipe 427 and the cooling water drain tube 106. Since the supply port and the drain port are separated to the front and rear of the housing 402, the cooling water circulates efficiently without stagnating in the housing 402. The guide unit 415 should preferably be made of hard and laser ray transmitting materials such as glass, polycarbonate, styrene, and acryl.

Embodiment 5

Next, it is described a fifth embodiment of the energy irradiation apparatus of the invention. The fifth invention has two sets of guide unit and optical fibers similar to those of the first embodiment. only the differences will be described below.

Figure 13:
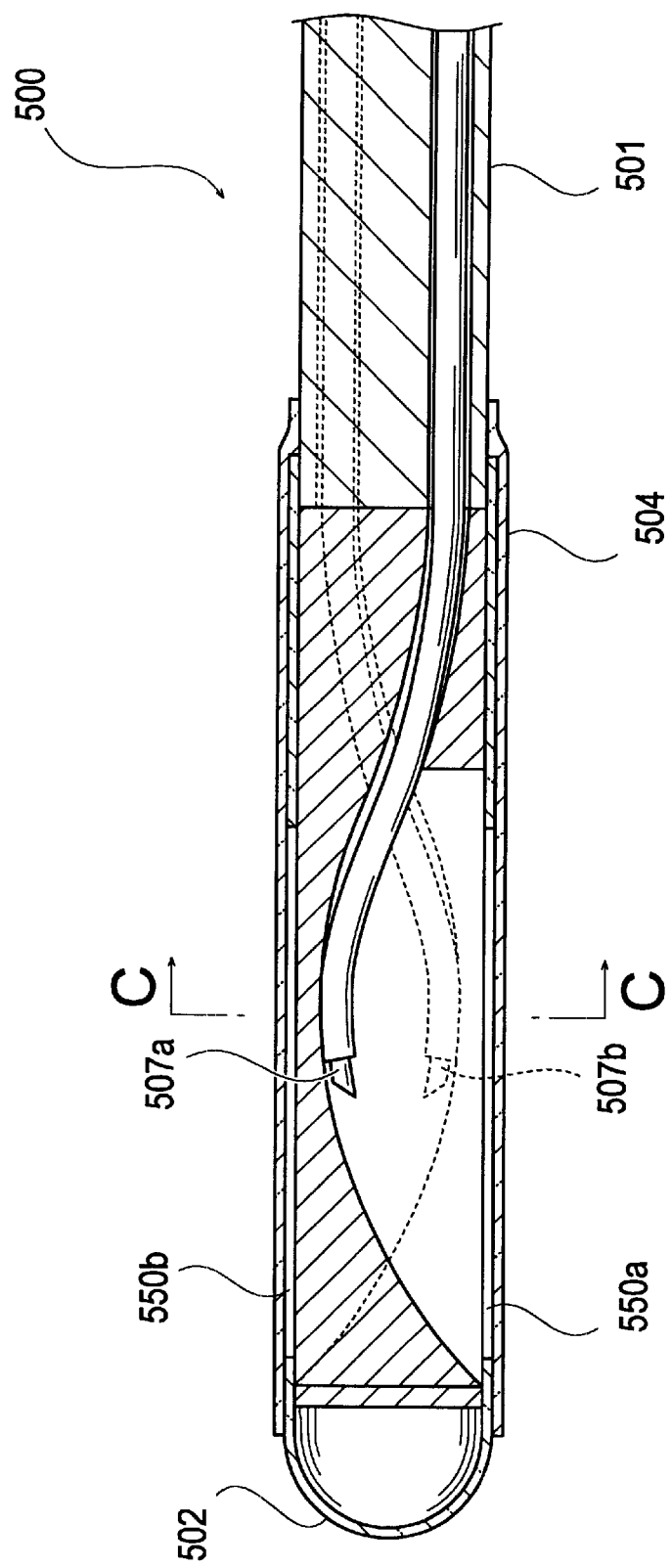
FIG. 13 is a cross-sectional view of the distal end of the laser irradiation apparatus of a fifth embodiment.
Figure 14:
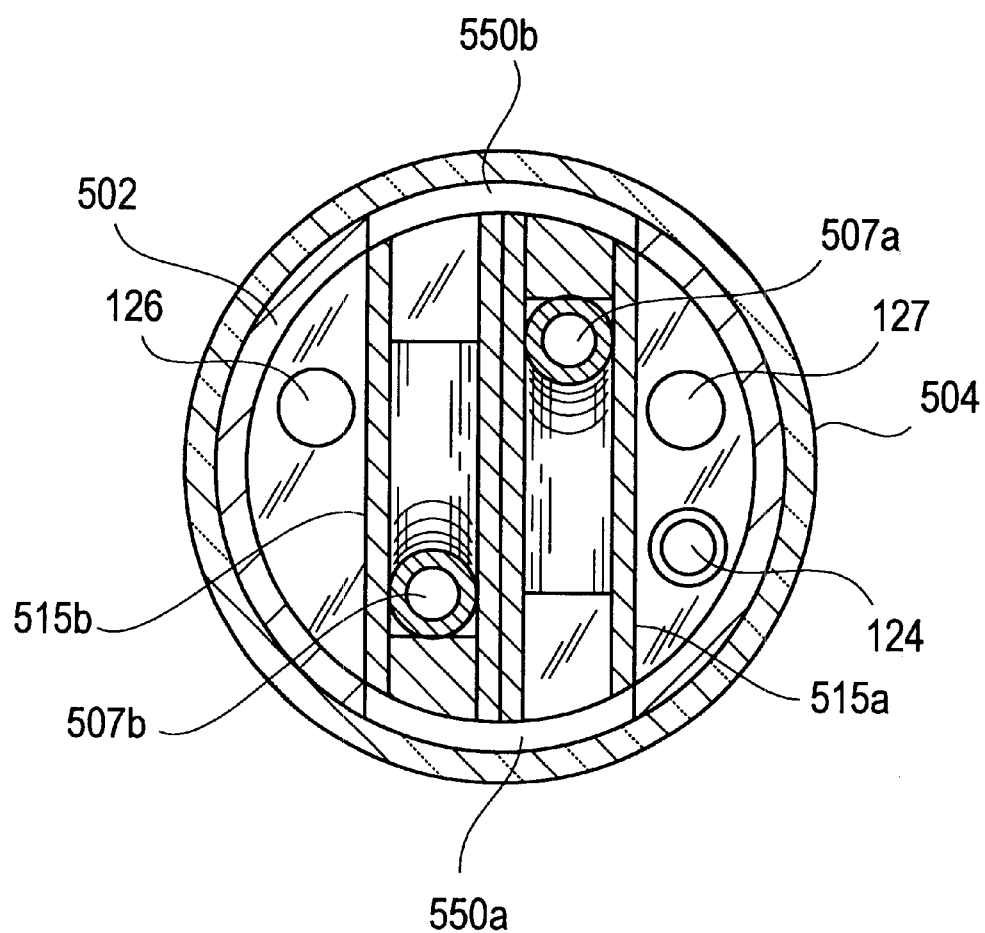
FIG. 14 is a cross-sectional view along the line C—C of the laser irradiation apparatus shown in FIG. 13.

FIG. 13 is a conceptual drawing showing two optical fibers at the distal end of a laser irradiation apparatus 500 according to the fifth embodiment, and FIG. 14 is a cross-sectional view along the line C—C of the laser irradiation apparatus shown in FIG. 13. A housing 502 of the laser irradiation apparatus 500 according to the fifth embodiment has laser emitting window 550a and 550b provided at two locations, one above the other in the figure. No balloon is provided and a cover 504 covers the entire periphery of the housing 502.

As can be seen from FIG. 14, guide units 515a and 515b are arranged in tandem inside the housing 502 in the fifth embodiment. The guide units 515a and 515b are both built identical to the guide unit 115 of the first embodiment. The guide unit 515b is placed 180 degrees opposite to the guide unit 515a. Optical fibers 507a and 507b are both built identical to the optical fiber 107 of the first embodiment. Both the optical fibers 507a and 507b reciprocate inside the guide units 515a and 515b respectively. The optical fibers 507a and 507b are driven by a drive unit that is connected to the proximate end of the main body 501 through separate lumens. The drive unit is constructed similarly as in the embodiment shown in FIG. 8, wherein the gripping joint 136 holds the two optical fibers together.

According to the fifth embodiment, the laser rays are emitted in two directions 180 degrees apart to each other simultaneously, so that it is possible to treat the left and right of the prostate surrounding the urethra simultaneously, thus shortening the operation time.

Embodiment 6

Figure 15:
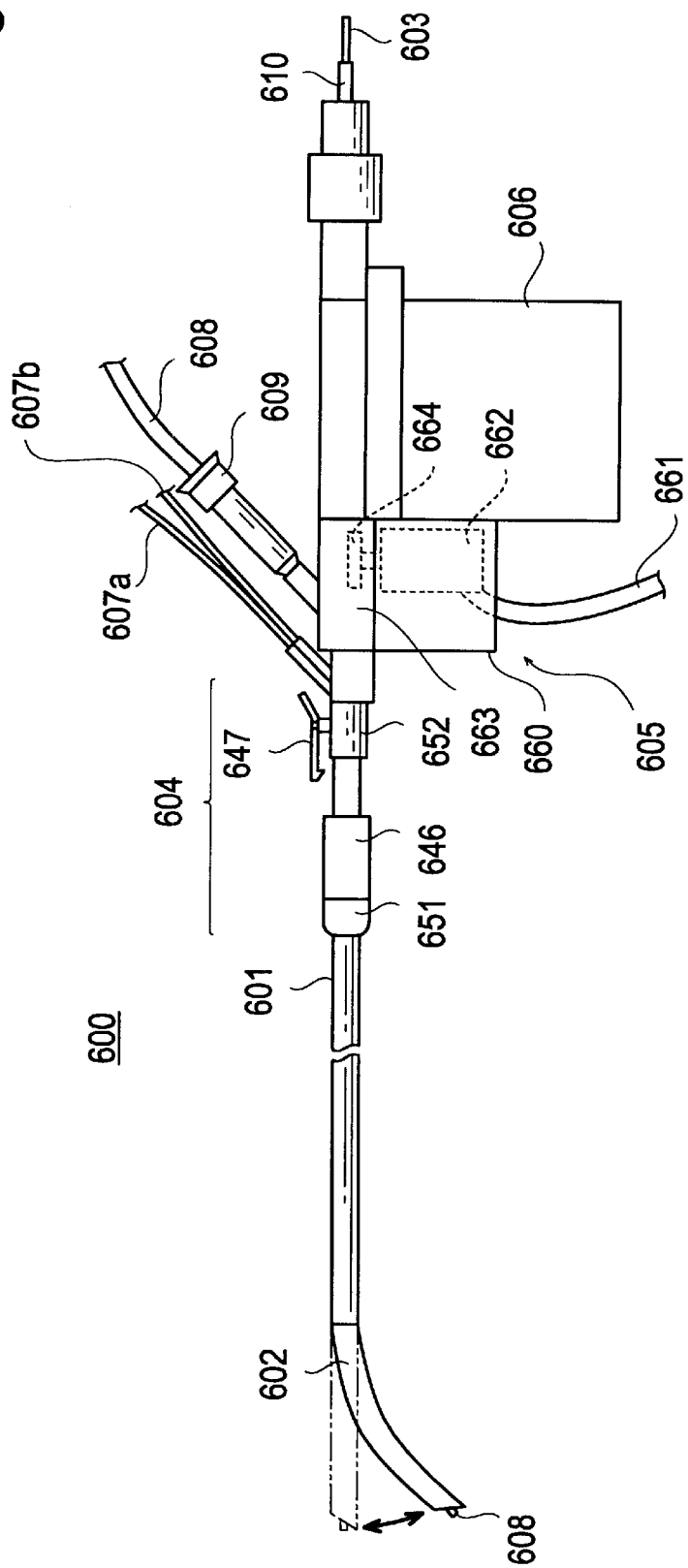
FIG. 15 is a schematic drawing of the laser irradiation apparatus of a sixth embodiment.

Refer to FIG. 15, a laser irradiation apparatus 600 is described below. The laser irradiation apparatus 600 according to the sixth embodiment is a side irradiating laser irradiation apparatus that irradiates vital tissues with laser rays, and is used for treating benign prostatic hyperplasia as the first embodiment.

The laser irradiation apparatus 600 comprises: a long and slender main body 601 made of a tube-like member; a flexible curving part 602 that is provided or attached to the distal end of the main body 601; an optical fiber 603 that is slidably provided inside the main body 601 and the curving part 602, receives incident laser rays through its proximate end, and emits said laser rays sideways or diagonally through its distal end; and a curving control unit 604 that forms the curving part 602 into a curved track with a specified curvature, along which the tip of the optical fiber 603 slides. The curving part 602 is curved by means of the curving control unit 604 after having been inserted into the body cavity. The laser irradiation apparatus 600 further has a drive unit 605 that causes the optical fiber 603 to reciprocate along the axial direction of the main body 601. A cushioning device 606 is provided adjacent to the driving unit 605.

In order to cool the surface of the vital tissue being irradiated by the laser rays as well as the inside of the curving part 602, cooling water is supplied to the inside of the curving part 602 from a coolant supply device (not shown) by means of the cooling water supply tube 607a. After circulating the curving part 602, it is discharged to the outside of the patient's body via a drain tube 607b.

An endoscope insertion port 609 is provided at the proximate end of the laser irradiation apparatus 600 in order to insert an endoscope 608. The endoscope 608 is inserted freely through the endoscope inserting port 609 into the main body 601.

Figure 16:
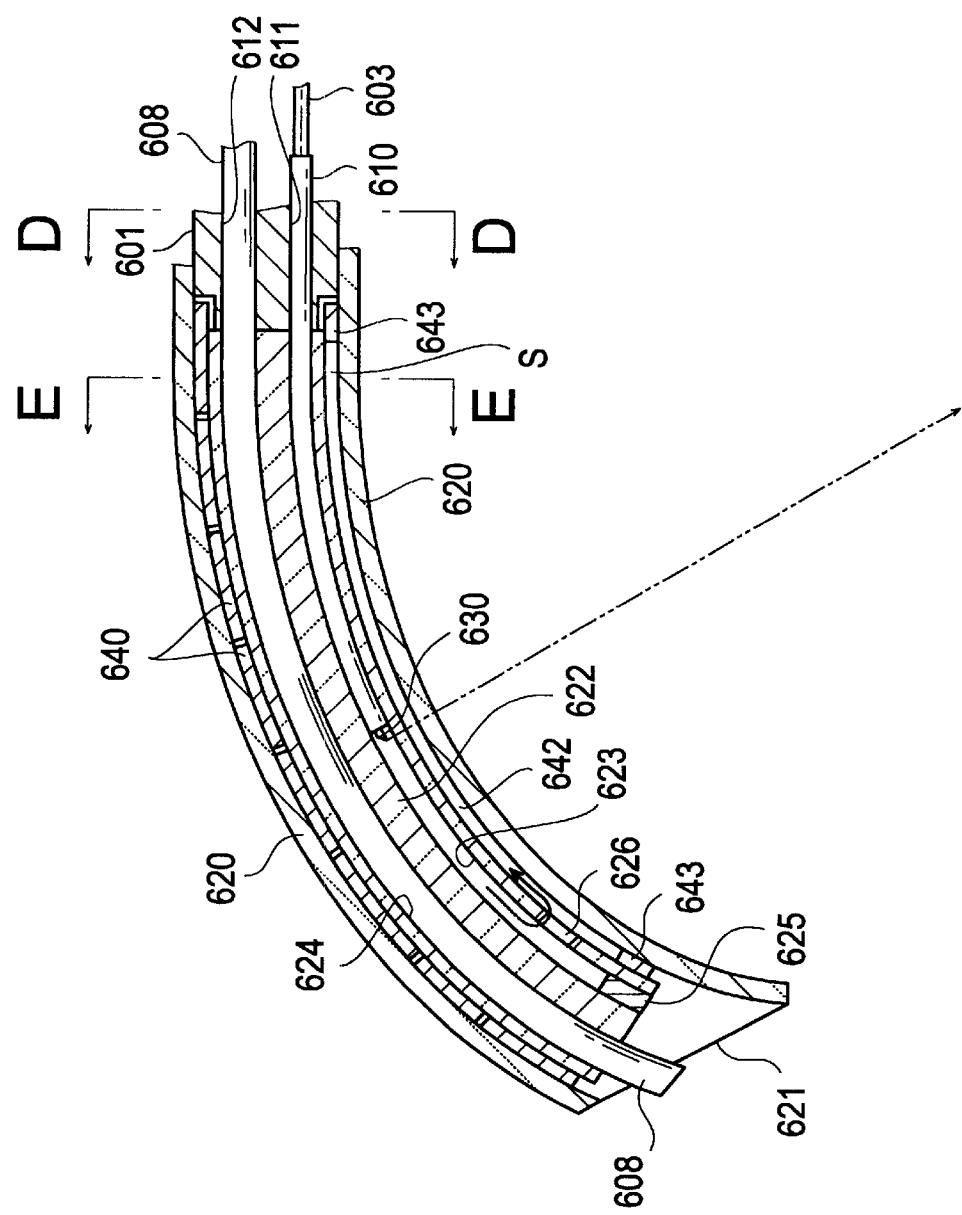
FIG. 16 is a cross-sectional view of the distal end of the laser irradiation apparatus of a sixth embodiment.
Figure 17:
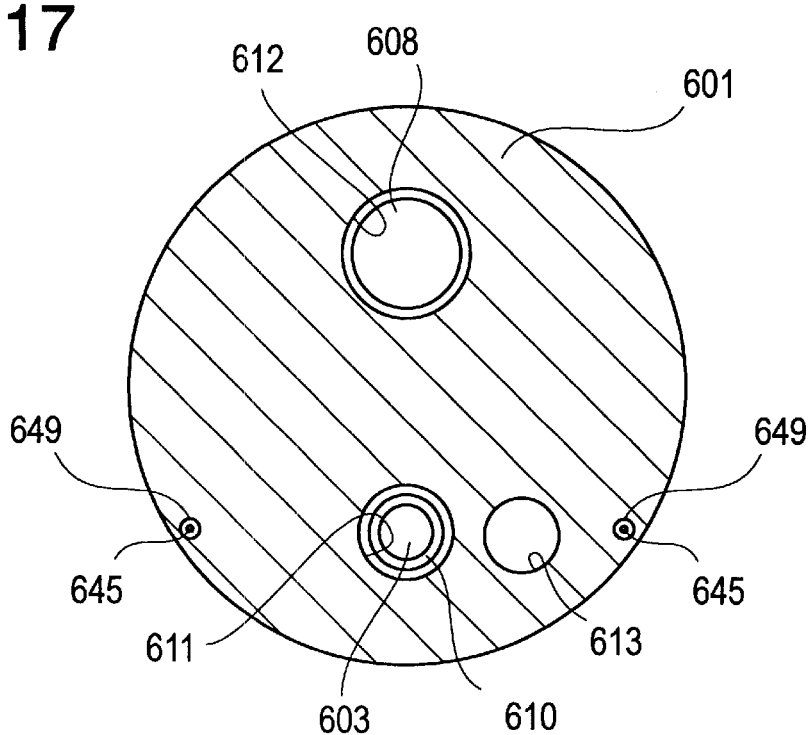
FIG. 17 is a cross-sectional view along the line D—D of the laser irradiation apparatus shown in FIG. 16.

More specifically, as shown in FIG. 16 and FIG. 17, the main body has a lumen 611, into which the optical fiber 603 covered by the protective tube 610 is inserted in such a way as to be able to move reciprocally, and a lumen 612, into which the endoscope 608 is inserted. The lumen 611 communicates with a lumen 623, which is formed by a soft tube 622 placed inside the curving part 602 as described later. The distal end of the lumen 623 is sealed by a sealing member 625. A through hole 626 is provided at the bottom side of soft tube 622 near the distal end in order to communicate with the lumen 623. The lumens 611 and 623 also function as lumens to guide the cooling water. The lumen 611 communicates with a coolant supply tube 607a and guides the cooling water to the curving part 602. The cooling water flows into a cooling drain lumen 613 formed in the main 601 via a through hole 626 and passing through the protective tube 620 that maintains a close contact with the vital tissue. The lumen 613 communicates with a coolant drain tube 607b. The lumens 611, 612, and 613 are formed in parallel with the axis of the main body 601.

In order to prevent water leakage, an O-ring (not shown) is provided to seal the gap between the protective tube 610 and the lumen 611. It is preferable to provide a check valve (not shown) in the lumen 611 provided for the coolant water guide. The temperature of the coolant not particularly specified as long as it is appropriate to reduce the damage of the fiber tip 630 of the optical fiber 603 and/or the damage on the surface of the vital tissue related to the irradiation of laser rays, but it should preferably be 0–37° C. or more specifically 8–25° C., which is less likely to get chilblain and is more efficient cooling effects. The cooling water is preferable to use a sterilized water, or more preferably physiological saline.

As shown in FIG. 16, the curving part 602 is covered by the protective tube 620. The protective tube 620 is made of a flexible soft material and does not prevent curving action of the curving part 602. The distal end of the protective tube 620 is open. In order to make it easier to insert it, the distal end of the protective tube 620 is formed into a slanted surface 621. A soft tube 622 made of a flexible soft material is provided inside the curving part 602. When the curving part 602 curves, the soft tube 622 also curves. The protective tube 620 and the soft tube 622 are made of light transmitting materials.

Figure 18:
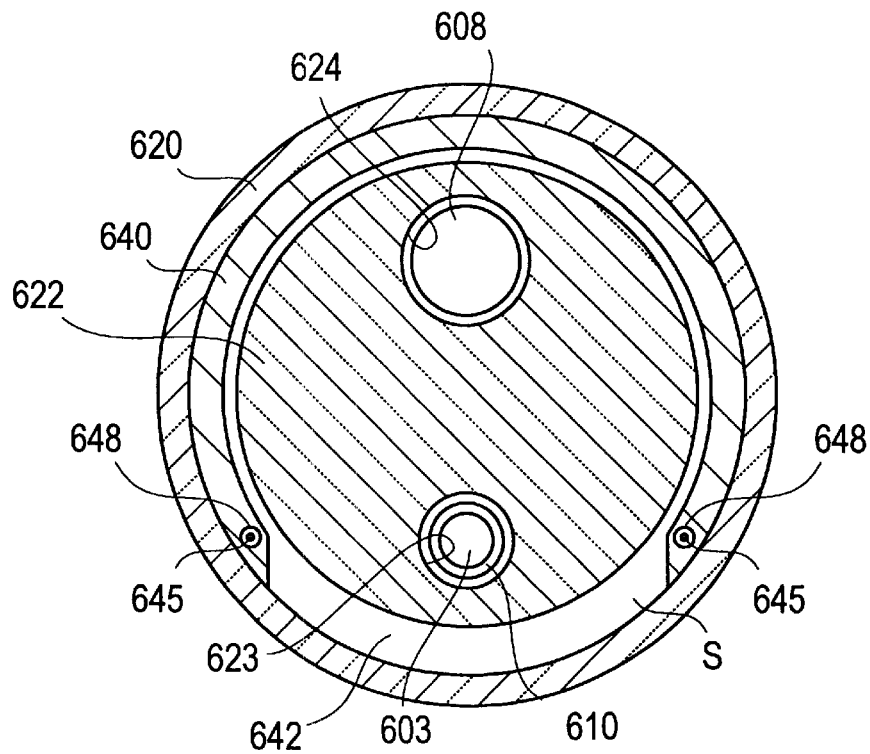
FIG. 18 is a cross-sectional view along the line E—E of FIG. 16.

As shown in FIG. 16 and FIG. 18, the soft tube 622 has the lumen 623, into which the optical fiber 603 is inserted in such a way as to be able to move reciprocally, and a lumen 624, into which the endoscope 608 is inserted. The lumen 623 communicates with the lumen 611 of the main body 601, and the lumen 624 communicates with the lumen 612 of the main body 601. The soft tube 622 has no lumen formed to communicate with the lumen 613 of the main body 601. The cooling water that has been guided by the lumen 611 and the lumen 623 flows into a gap or space S formed between the soft tube 622 and the protective tube 620 via the through hole 626 that communicates with the lumen 623, and is discharged to the outside of the patient's body via the lumen 613 and the cooling water drain tube 607b. As a result of such circulation of the cooling water, the heating of the fiber tip 630 is suppressed to keep the normal tissue in contact with the curving part 602 cooled, while allowing only the deep area to be heated.

The endoscope 608 is inserted into the lumen 612 and the lumen 624 in such a way as to make it slidable. The endoscope 608 consists of an optical fiber bundle and a protective tube and has an image formation lens (not shown). With the help of the endoscope observation, the position of the curving part 602 and the position of the laser irradiation can be visually confirmed.

The optical fiber 603 is inserted in the lumen 611 and the lumen 623 in such a way to be able to slide freely for transmitting the laser rays. The optical fiber 603 is covered by the protective tube 610 except the vicinity of the distal end. The proximate end of the optical fiber 603 is connected to a laser generator (not shown) via an optical connector.

Figure 19:
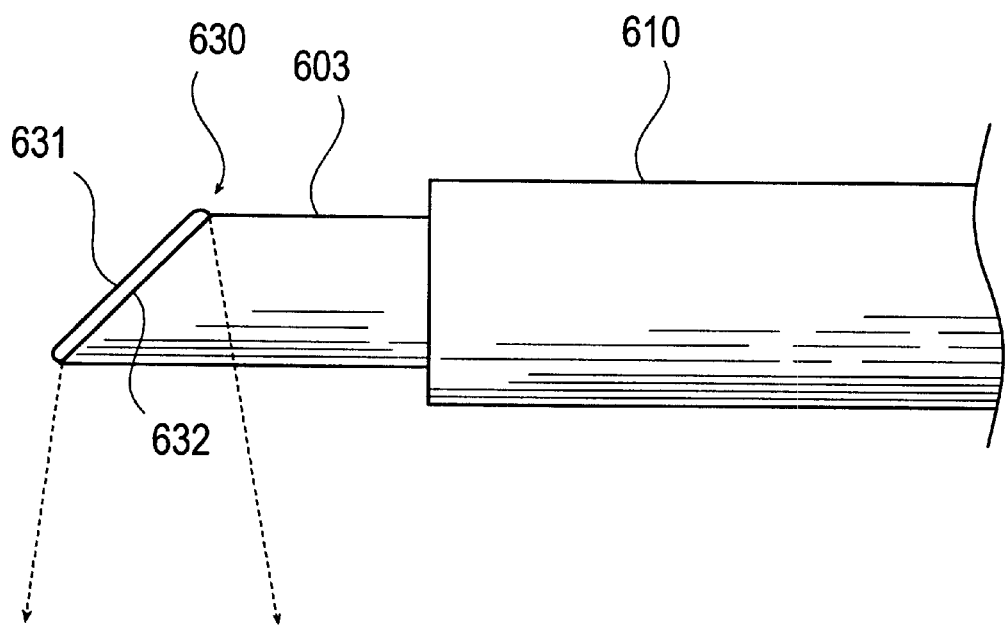
FIG. 19 is a detail view of the distal end of the optical fiber in the sixth embodiment.

Refer to FIG. 19, the fiber tip 630 of the sixth embodiment has a flat face 631, which is slanted relative to the lengthwise direction of the optical fiber 603. The slant angle of the flat face 631 is approximately 35–50 degrees, preferably 45 degrees relative to the central axis of the optical fiber 603. The flat face is formed in a smooth plane. The flat face is coated with a reflective film 632. The reflective film 632 is identical to the reflective film 114 of the first embodiment. The laser rays, having been transmitted through the optical fiber 603, are reflected by the reflecting film 632 at the fiber tip 630 and are emitted sideways of the fiber as shown with dotted line arrows in the drawing.

Next, it is described in details about the constitutions of the curving part 602 and the curving control unit 604.

As shown in FIG. 20, the curving part 602 of this embodiment consists of multiple knotty rings 640 arranged to form a hollow tube-like shape. A connecting part 641 is formed on the proximate end-side edge of each knotty ring 640. Each of them is rotatably linked via the connecting part 641 and pins with another connecting ring 640 located on the proximate end-side. The knotty ring 640 closest to the proximate end of the entire link has no connecting part 641 is formed and is affixed to the distal end of the main body 601. As shown in FIG. 18, each knotty ring 640 has an arc shape on the cross section perpendicular to the axis and has a laser emitting window 642 formed on the bottom side in the drawing. The laser rays pass through this emitting window 642 and radiate on the lesion. The knotty rings 640 located on both ends have the laser ray emitting window 642 as well as a ring part 643. Both ends of the soft tube 622 are supported by these ring parts 643.

Figure 20A:
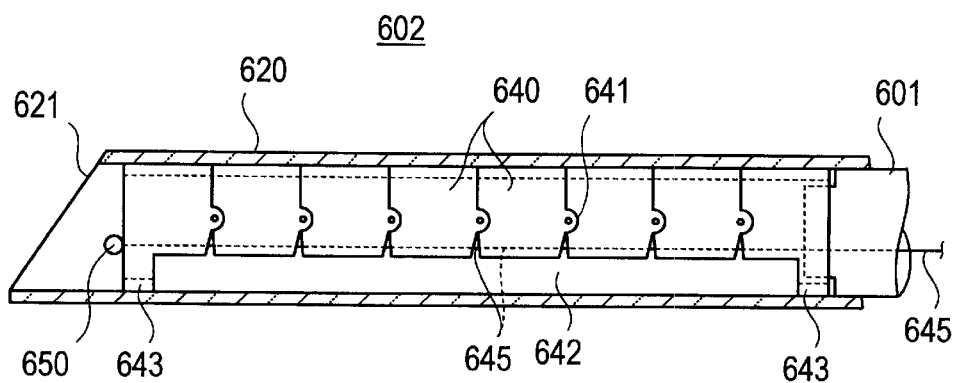
FIGS. 20A and 20B are drawings to show the curving motion of the curving part, wherein FIG. 20A indicating the original condition, and FIG. 20B indicating the condition after curving.

As shown in FIG. 20 and FIG. 21, the curving control unit 604 comprises a pull wire 645 that extends from the farthest knotty ring 640 through each knotty ring 640, a slider 646 that is slidably attached to the main body 601 and is connected to the rear end of the pull wire 645, and a locking pin 647 that restricts the position of the slider 646.

A hole 648 is formed on both sides of the bottom of each knotty ring 640 and the pull wire 645 is put through each hole 648 (refer to FIG. 18). A pair of holes 649 are formed on the main body 601, through which the pull wire 645 is put (refer to FIG. 17). Since the pull wire is not exposed in the laser emitting window 642, it does not affect the passage of the laser rays. At the distal end of the pull wire 645, after it has passed the farthest knotty ring 640, is provided a slip-off preventing member 650.

Figure 20B:
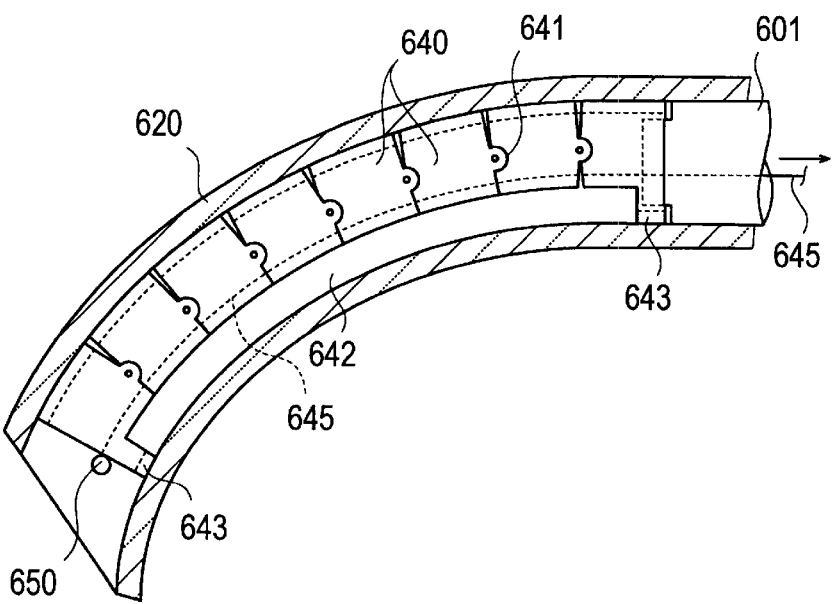

When the pull wire 645 is pulled toward the proximate end side as shown in FIG. 20B with an arrow, the knotty rings 640 rotates in such a way that the distal end tilts downward because the pull wire 645 is located below the connecting part 641 on each knotty ring. Since the pull wire 645 passes through each knotty ring 640 in a balanced manner between the left and right sides in the cross section perpendicular to the axis, each knotty ring 640 rotates without tilting left or right in the cross section perpendicular to the axis. Thus, the curving part 602 can be operated to curve with a specified curvature.

Furthermore, when the main body 601 is pulled out while the locking pin 647 is released from affixing of the slider 646, the curving part 602 returns to its initial straight condition (as shown in FIG. 20A). Therefore, in the example shown here, no wire is provided for enforcing the once curved curving part 602 to restore its initial status. However, it is possible to provide a restoring wire, in which case a single wire passing through the upper part of the knotty rings 640 will suffice the purpose.

Figure 21A:
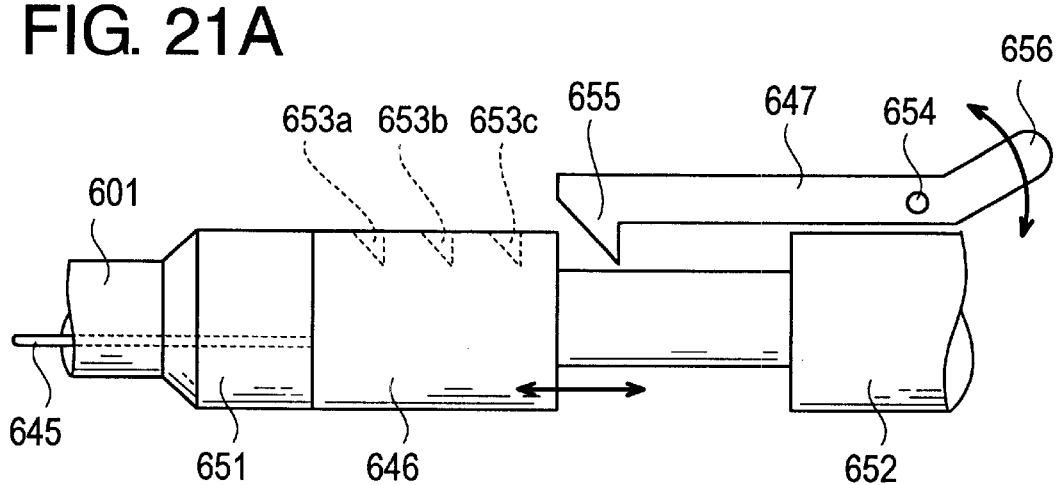
FIGS. 21A and 21B are drawings to show the curving control mechanism.
Figure 21B:
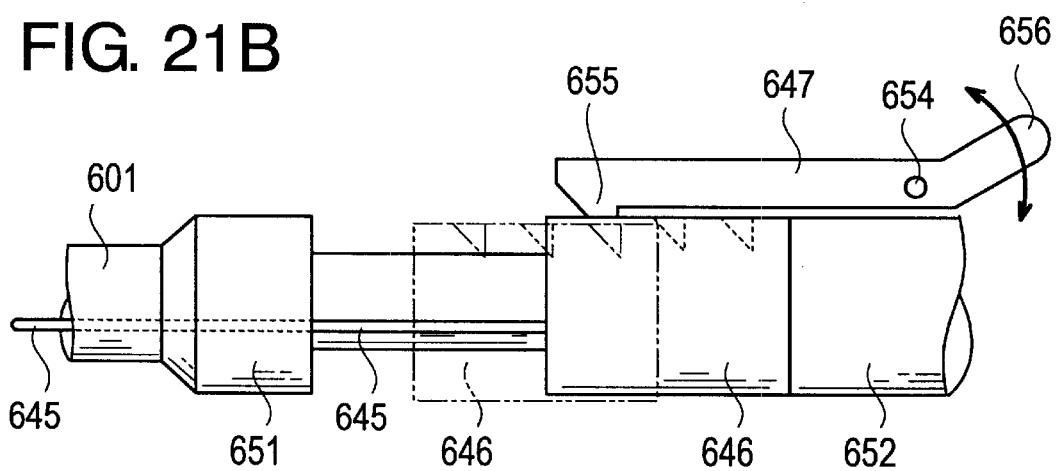
Figure 21C:
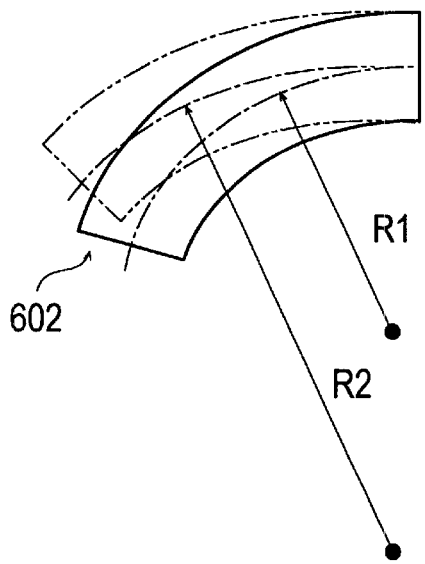
FIG. 21C is a drawing f or describing the curving condition of the curving part.

As shown in FIG. 21A and FIG. 21B, the slider 646 can slide freely between the first stopper 651 and the second stopper 652 affixed to the main body 601. Multiple (three in this case) notches 653 (653*a*, 653*b*, 653*c*) are formed on the upper surface of the slider 646. The locking pin 647 is provided on the upper surface of the second stopper 652 to be rotatable around a shaft 654. At the distal end of the locking pin 647, a locking pawl 655 is provided to engage with the notches 653 (collective name for 653*a*, 653*b*, 653*c*), and its rear part constitutes a releasing arm 656, which is pushed down when it is desired to release the engagement between one of the notch 653 and the locking pawl 655. The locking pin 647 is provided with a spring mechanism (not shown) to energize the locking pin 647 to rotate counter-clockwise around a shaft 654. The engaged condition between the notch 653 and the locking pawl 655 is maintained by a spring force of the spring mechanism.

In the case shown here, the distance pulled by the pull wire 645 connected to the slider 646 is variable in three steps by means of selecting a proper one of the notches 653 for engagement with the locking claw 655. By doing so, the curvature of the curving part 602 can be changed in three steps. In other words, if the locking claw 655 is engaging with the leftmost notch 653a as shown with solid lines in FIG. 21B, the largest pulling distance of the pull wire 645 results. As a result, the curvature of the curving part 602 is the largest (the radius of curvature R1 is the smallest) as shown with solid lines in FIG. 21C. On the other hand, if the locking claw 655 is engaging with the rightmost notch 653*c* as shown with phantom lines in FIG. 21B, the pulling distance is the smallest. As a result, the curvature of the curving part 602 is smallest (the radius of curvature R2 is largest) as shown with phantom lines in FIG. 21C.

When the curving part 602 is curved into a specified curvature by operating the curving control unit 604, the soft tube 622 in the curving part 602 also curves. The lumen 623 of the curved soft tube 622 forms the track along which the tip of the optical fiber 603 slides. The curved track is an arc-shaped track and the fiber tip 630 is on the arc-shaped track while it is reciprocating.

Said drive unit 605 comprises a motor 662 that is enclosed in a casing 660 and is powered by means of an electric cable 661 as shown in FIG. 15, and a cam box 663 that converts the rotary motion of the motor 662 into the reciprocating motion. The motor 662 can be used an induction motor, a servomotor, a stepping motor, etc. The mechanism for reciprocating the optical fiber 603 is identical to that of the first embodiment. The stroke, i.e., the range of the reciprocating motion, of the fiber tip 630 is twice the rotating radius of the joint 167 as shown in FIG. 9.

Figure 22:
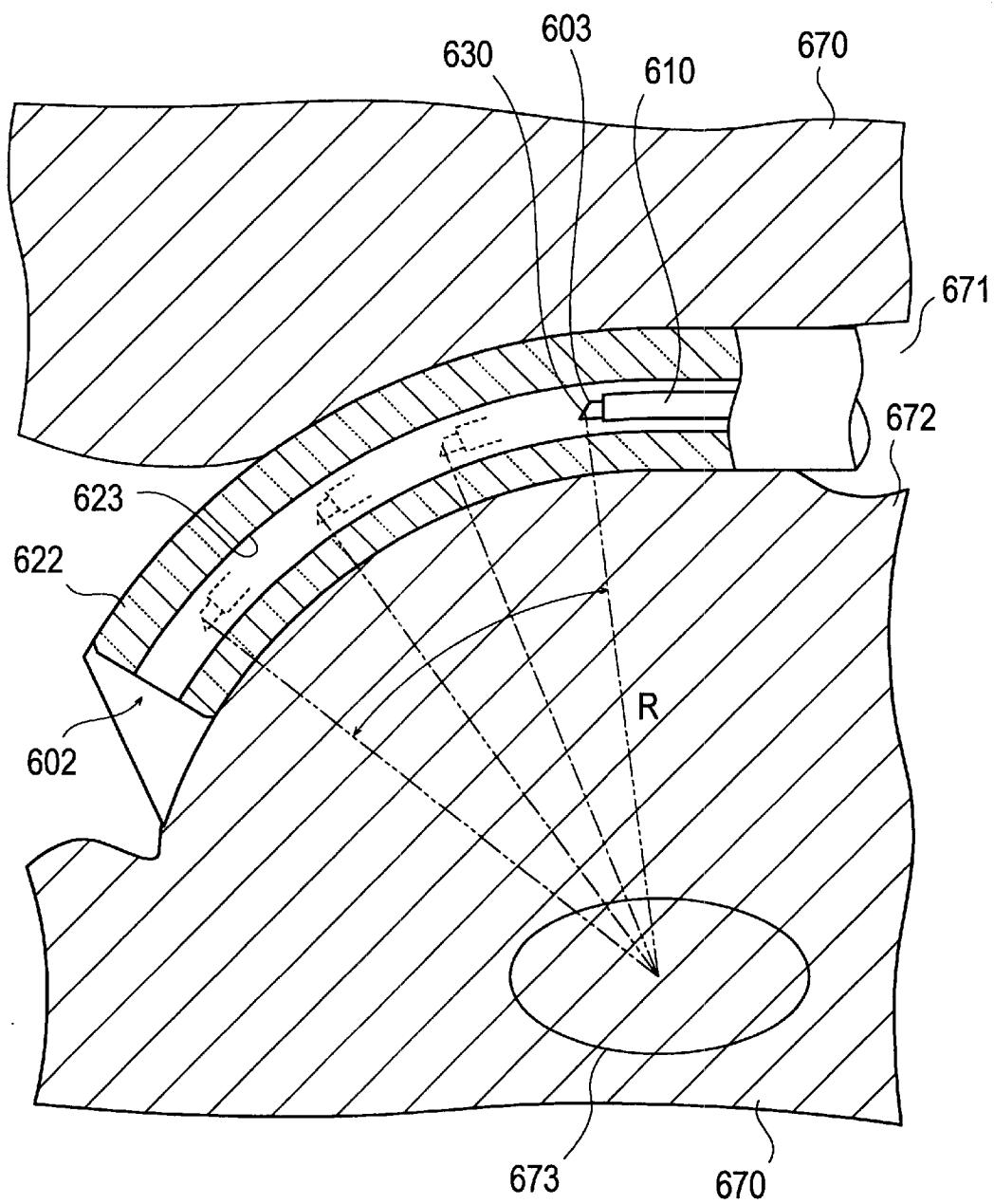
FIG. 22 is a schematic diagram showing an actual treatment for describing the changes in the irradiating direction of the laser ray in coordination with the optical fiber's movement.

In FIG. 22, the parts other than the optical fiber 603 and the soft tube 622 are simplified, and "670" is a cross sectional of the prostate. The curving part 602 is curved to a specified curvature after it is inserted into the urethra 671 by means of operating the curving control unit 604. This will cause the curving part 602 to contact closely with the urethra surface 672 and the soft tube 622 to curve as well forming a curved track along which the fiber tip 630 slides. It can also be configured to have a balloon to cause the curving part 602 to contact the urethra surface 672.

The fiber tip 630 reciprocates driven by the drive unit 605 within a stroke length, which is a part of the curved track shown by the arrow. When the fiber tip 630 is located closest to the proximate end, it must be on the distal end side of the most proximate side knotty ring 640, and it mustn't be beyond the furthest knotty ring 640 when it is located at its distal end.

The laser rays are irradiated from the fiber tip 630 sideways (preferably approximately perpendicular) relative to the axial direction of the optical fiber 603. The axial direction of the optical fiber 603 is the tangential direction of the arc formed by the curving part 602 regardless of the position of the fiber tip 630. As a result, the irradiating laser rays always head toward the vicinity of the center of the circle that includes this arc (target area 673).

By irradiating the laser rays while the optical fiber 603 is being reciprocated, the position irradiated by the laser rays change constantly on the surface 672 of the vital tissue existing above the target area 673 in the figure, so that the laser ray irradiation time is short, the energy provided by the laser rays is dispersed, and the heat generation is small. Similarly, the laser irradiation time is short and the heat generation is limited in the area below the target area 673 in the figure. On the other hand, there is an energy concentration and a sufficient amount of heat is generated for the purpose of heating to diminish the legion in the target area 673 existing deep inside the vital tissue.

Therefore, this technique solves the problem of the prior art that "the laser irradiation has to be limited to a level that does not affect the urethra surface 672 by heating" due to the fact that the laser rays were irradiated from a fixed laser irradiation part. In other words, the laser rays emitted from the constantly moving fiber tip 630 concentrate on the target area 673, so that the surrounding area (normal tissue) outside of the target area 673 is maintained at relatively low temperatures and be protected from the effect of the laser rays. This laser irradiation apparatus 600 offers high safety to the patient because damage to the areas other than the target area 673 are prevented or reduced. It is particularly advantageous as the surface layer damages are prevented even when the target area 673 is located at a position deep inside the vital tissue.

The arc that the fiber tip 630 is generating is smaller than a half circle similar to the case of the first embodiment, and is preferably 8–25% of a circle assuming a half circle is expressed as 50%. The radius R of the arc is adjusted depending on the depth of the target area or the diameter of the main body 601. In case of an apparatus intended for the treatment of benign prostatic hyperplasia, the diameter of the main body 601 should preferably be 5–8 mm, and the applicable depth of the target area is approximately 10–20 mm. The radius of curvature R is adjusted according to the depth of the target area by means of the curving control unit 604.

It is described now the operating procedure of the laser irradiation apparatus 600 referring to FIG. 22.

First, insert the main body 601 into a body cavity and locate the curving part 602 on the surface layer above and in the vicinity of the target area 673, which is the legion, i.e., the location to be heated. It is preferable to confirm directly the position of the curving part 602 by means of the endoscope 608. The target point position in the length wise direction of the body cavity can be adjusted by means of moving the main body 601 manually along the lengthwise direction, and the position in the circumferential direction of the body cavity can be adjusted by means of rotating the main body 601 manually.

When the positioning of the target point is completed, the operator selects one of the three curvatures of the curving part 602 by means of the curving control unit 604 depending on the condition of benign prostatic hyperplasia. For example, if the target area 673 is located in the surface layer close to the urethra surface 672, move the slider 646 to make the locking claw 655 engage with the leftmost notch 653a (as shown by solid lines in FIG. 21B) in order to increase the curvature of the curving part 602 (reduce the radius of curvature R1). On the other hand, if the target area 673 exists in a deep area relatively far from the urethra surface 672, move the slider 646 to make the locking claw 655 engage with the rightmost notch 653c (as shown by phantom lines in FIG. 21B) in order to reduce the curvature of the curving part 602 (increase the radius of curvature R2).

Operate the laser irradiation apparatus, guide the generated laser rays to the curving part 602 via the optical fiber 603, and irradiate the target point with the laser rays emitting from the fiber tip 630. At this time, the cooling water is supplied to cool the urethra surface 672. The fiber tip 630 reciprocates in the axial direction by means of the drive unit 605 at the cycle of 0.1–10 Hz, preferably 1–6 Hz. The optical axis of the laser rays changes continuously but always cross the target point. As a result, it is possible to heat and cure only the target area 673 located deep inside the tissue while protecting the vital tissue surface 672.

Next, change the target position by moving the main body 601 lengthwise and/or rotating it in the circumferential direction. When this position adjustment is completed, start the laser irradiation again. By repeating this operation as many times as needed, a relatively wide target area 673 can be heated.

The laser irradiation apparatus 600 of this embodiment has advantages such that it has a simpler structure, can be manufactured easily and is less likely to break down.

The numerical aperture of the optical fiber 603 should be less than 0.4, more preferably less than 0.3.

If the irradiating laser rays are emitted at a low numerical aperture, it is possible to increase further the energy density of the laser rays in the area of the target point and its vicinity. The laser rays used can be anything as long as they have deep penetration capabilities, but it is preferable that the laser rays have the wavelengths of about 750–1300 nm or more preferably about 1600–1800 nm similar to those of the first embodiment.

The outside diameter of the main body 601 is not specified particularly as long as it can be inserted into the body cavity. However, the outside diameter of the main body 601 should be preferably 2–20 mm, or more preferably 3–8 mm.

The main body 601 should be made of the same kind of materials cited in the first embodiment. The surface of the main body 601 can be coated with a material of a low friction coefficient such as silicon, fluorocarbon resin, etc., or a lubricating film containing hydrophilic polymer materials as mentioned in the first embodiment.

The soft tuber 622 into which the optical fiber 603 is inserted and the protective tube 620 that covers the curving part 602 should be made of materials with excellent laser ray transmitting capabilities such as: acryl; polystyrene; polycarbonate; polyethylene; polypropylene; vinylidene chloride; polyethylene terephthalate; and polybutylene terephthalate. The soft tube 622 and the protective tuber 620 are not necessary to be made entirely of materials that are laser ray transmitting, but rather only the areas that correspond to the laser emitting window 642 have to be made of materials that are laser ray transmitting.

The fiber tip 630 does not have to be a plate with a flat reflective surface, but rather it can be made of prisms and wedge plates.

Although the curving part 602 consisting of knotty rings 640 was shown in the above, the invention is not limited to such a case, but rather the curving part 602 can be a structure of any other kinds as long as it is capable of forming a curve. The curving direction does not have to be in a single direction, but rather it can be curved in multiple directions. Although the example above shows the curving control unit 604, which is capable of changing the curvature of the curving part 602 in several steps, it is also possible to design in such a way as to change the curvature of the curving part 602 steplessly by providing a means of winding up the pull wire 645.

One example condition of the laser irradiation apparatus 600 used for treating benign prostatic hyperplasia is as follows:

Effective length of the main body 601: 400 mm

Diameter of the main body 601: 4–7 mm (preferably 5 mm)

Laser source: Semiconductor laser (wavelength: 800–920 nm, continuous wave)

Optical fiber 603: Pure quartz fiber (core diameter: 400 $\mu$m, numerical aperture NA=0.37)

Laser irradiating direction: Emit laser rays perpendicular to the lengthwise direction (sideway irradiation)

Repetitive moving distances of the fiber tip 630: 20 mm (speed: 2 Hz)

Depth of the deep convergence point from the urethra: 10, 15, 20 mm

Surface layer coolant: Physiological saline (250 ml/min, 0° C.)

Radius of curvature of the track along which the fiber tip 630 slides: Three steps of 12.5, 17.5, and 22.5 mm (when the diameter of the main body 601 is 5 mm; arranged around the optical fiber 603).

It is obvious that this invention is not limited to the particular embodiments shown and described above but may be variously changed and modified without departing from the technical concept of this invention.

What is claimed is:

1. Laser irradiation apparatus, comprising:

a long and slender main body;

an optical fiber slidably provided inside said main body, which accepts incident laser rays through its proximate end and emits said laser rays sideways or diagonally through its distal end; and a guide unit that forms a curved track for the distal end of said optical fiber to slide, the distal end of said optical fiber being reciprocable within a stroke length which is a part of said curved track.

2. Laser irradiation apparatus according to the claim 1, wherein said laser rays are irradiated on vital tissues while the distal end of said optical fiber slides along the curved track.

3. Laser irradiation apparatus according to the claim 1, further comprising an endoscope built into said main body.

4. Laser irradiation apparatus according to the claim 1, wherein said guide unit forms a curved guide surface to guide the distal end of said optical fiber.

5. Laser irradiation apparatus according to the claim 1, wherein said guide unit consists of a box-like member.

6. Laser irradiation apparatus according to the claim 1, wherein said guide unit consists of a cylinder-like member.

7. Laser irradiation apparatus according to the claim 1, wherein said optical fiber has a reflecting part that reflects the laser rays sideways or diagonally.

8. Laser irradiation apparatus according to the claim 7, wherein said reflecting part has a reflecting film formed to reflect the laser rays.

9. Laser irradiation apparatus according to the claim 7, wherein said reflecting part is constituted by forming the distal end of said optical fiber in a flat face slanted relative to the lengthwise direction of said optical fiber.

10. Laser irradiation apparatus according to the claim 7, wherein said reflecting part comprises a reflective mirror provided at the distal end of said optical fiber.

11. Laser irradiation apparatus according to the claim 1, wherein said curved track includes a track with a shape of an arc smaller than a half circle.

12. Laser irradiation apparatus according to the claim 1, further comprising a drive unit that reciprocates said optical fiber along the axial direction of said main body.

13. Laser irradiation apparatus according to the claim 12, wherein said drive unit causes said optical fiber to reciprocate within a part of said curved track as its stroke length.

14. Laser irradiation apparatus according to the claim 1, wherein multiple sets of said optical fiber and said guide unit are provided.

15. Laser irradiation apparatus according to the claim 14, wherein said multiple optical fibers irradiate laser rays into different directions.

16. Laser irradiation apparatus according to the claim 1, further comprising a passage for supplying coolant that is used to cool the surface irradiated by the laser rays.

17. Laser irradiation apparatus according to the claim 1, wherein said guide unit is capable of adjusting said curved track's curvature.

18. Laser irradiation apparatus according to the claim 17, wherein said guide unit comprises:

a flexible curving part provided at the distal end of said main body; and a curving control mechanism for forming a curved track along which the distal end of said optical fiber slides.

19. Laser irradiation apparatus, comprising:

a long and slender main body;

a flexible curving part provided at the distal end of said main body;

an optical fiber slidably provided inside said main body and said curving part, which accepts incident laser rays through its proximate end and emits said laser rays sideways or diagonally through its distal end; and a curving control mechanism for forming a curved track along which the distal end of said optical fiber slides, the distal end of said optical fiber being reciprocable within a stroke length which is a part of said curved track.

20. Laser irradiation apparatus according to the claim 19, wherein said curving part forms, when it is curved, a curved guide surface along which the distal end of said optical fiber slides.

21. Laser irradiation apparatus according to the claim 19, wherein said curving part has a curvature that is variable.

22. Laser irradiation apparatus according to the claim 19, wherein said curving part consists of multiple rings, which are linked together.

23. Laser irradiation apparatus according to the claim 19, wherein said curving control mechanism can adjust the curved track's curvature.

* * * * *